(12) United States Patent
Odom

(10) Patent No.: US 6,861,559 B2
(45) Date of Patent: Mar. 1, 2005

(54) IMINOAMINES AND PREPARATION THEREOF

(75) Inventor: Aaron L. Odom, Lansing, MI (US)

(73) Assignee: Board of Trustees of Michigan State University, East Lansing, MI (US)

(*) Notice: Subject to any disclaimer, the term of this patent is extended or adjusted under 35 U.S.C. 154(b) by 0 days.

(21) Appl. No.: 10/315,269

(22) Filed: Dec. 10, 2002

(65) Prior Publication Data

US 2004/0110983 A1 Jun. 10, 2004

(51) Int. Cl.$^7$ .......................... C07F 7/28; C07C 249/02; C07C 251/12; C07C 251/14; C07C 251/16
(52) U.S. Cl. ..................... 564/272; 273/275; 273/277; 273/279; 556/51
(58) Field of Search ........................ 564/272, 273, 564/275, 277, 279; 556/51

(56) References Cited

PUBLICATIONS

Database CAPLUS on STN, Acc. No. 1979:134301, Alvager et al., Advances in Experimental Medicine and Biology (1978), 97 (Pharmacol. Intervention Aging Process), p. 293–6 (abstract).*
Becker et al., Journal of Organic Chemistry (1969), 34(12), p. 4162–4.*
Database CAPLUS on STN, Acc. No. 1968;38739, Feldmann et al., Zeitschrift fuer Naturforschung, Teil B: Anorganische Chemie, Organische Chemie, Biochemie, Biophysik, Biologie (1967), 22(7), p. 722–31 (abstract).*
Database CAPLUS on STN, Acc. No. 1982:122764, Lloyd et al., Journal of Chemical Research, Synopses (1981), 11, p. 356 7 (abstract).*
Schrieber, Science 287: 1964–1969 (2000.
Spring et al., J. Am. Chem. Soc. 124: 1354–1363 (2002).
Ding et al., J. Am. Chem. Soc. 124: 1594–1596 (2002).
Hsieh–Wilson et al., Acc. Chem. Res. 29: 164–170 (1996).
Johnson and Bergman, J. Am. Chem. Soc. 123: 2923–2924 (2001).
Siebeneicher and Doye, J. Prakt. Chem. Ztg. 341: 102–106 (2000).
Haak et al., Angew. Chem. Int. Ed. 38: 3389–3391 (1999).
Bytschkov and Doye, Eur. J. Org. Chem. 4411–4418 (2001).
Shi et al., Organometallics 21: 3967–3969 (2001).
Ong et al., Organometallics 21: 2839–2841 (2002).
Ackermann and Bergman, Org. Lett. 4: 1475–1478 (2002).
Doye and Siebeneicher, Eur. J. Org. Chem. 1231–1240 (2002).
Heutling and Doye, J. Org. Chem. 67: 1961–1964 (2002).
Haak et al., Eur. J. Org. Chem. 457–463 (2002).
Cao et al., Org. Lett. 4: 2853–2866 (2002).
Davis and Yelland, J. Am. Chem. Soc. 59: 1998–1999 (1937).
Saegusa et al., J. Org. Chem. 36: 2876–2880 (1971).
Bestchart and Hegedus, J. Am. Chem. Soc. 114: 5010–5017 (1992).
Harris et al., In Inorg. Che. 40: 1987–1988 (2001).
Straub and Bergman, Angew. Che. Int. Ed. 40: 4632–4635 (2001).
Walsh et al., J. Am. Chem. Soc. 114: 1708–1719 (1992).
Sweeney et al., Agnew. Chem. Int. Ed. 39: 2339–2343 (2000).
Polse et al., J. Cm. Chem. Soc. 120: 13405–13414 (1998).
Baranger et al., J. Cm. Chem. Soc. 115: 2753–2763 (1993).
Pohlki and Doye, Agnew. Chem. Int. Ed. 40: 2305–2308 (2001).
Tillack et al., Agnew. Chem. Int. Ed. 41: 2541–2543 (2002).
Raines and Kovacs, J. Heterocyclic Chem. 7: 233 (1970).
Cao et al., Organometallics 20: 5011–5013 (2001).
Kakaliou et al., Inorg. Chem. 38: 5964–5977 (1999).
Fekl and Goldberg, J. Am. Chem. Soc. 124: 6804–6805 (2002).
Spencer et al., J. Am. Chem. Soc. 124: 2108–2109 (2002).
Smith et al., J. Am. Chem. Soc. 123: 9222–9223 (2002).
Dai and Warren, Chem. Commun. 1998–1999 (2002).
Bourget–Merle et al., Chem. Rev. 102: 3031–3066 (2002).
Brady and Shieh, J. Org. Chem. 48: 2499–2502 (1983).

* cited by examiner

*Primary Examiner*—Brian Davis
(74) *Attorney, Agent, or Firm*—Ian C. McLeod

(57) ABSTRACT

A process is described for producing one or more substituted iminoamines, in particular β-unsaturated β-iminoamines, in a single reaction comprising reacting one or more primary amines, alkynes, and isonitriles in the presence of a transition metal catalytic complex, preferably a titanium metal catalytic complex such as (N,N-di(pyrrolyl-α-methyl)-N-methylamine)titanium (Ti(NMe$_2$)$_2$(dpma)), under reaction conditions effective for 3-component coupling of the primary amines, alkynes, and isonitriles to produce one or more of the substituted iminoamines.

56 Claims, No Drawings

IMINOAMINES AND PREPARATION THEREOF

CROSS-REFERENCE TO RELATED APPLICATION

Not applicable.

STATEMENT REGARDING FEDERALLY SPONSORED RESEARCH OR DEVELOPMENT

Not applicable.

REFERENCE TO A "COMPUTER LISTING APPENDIX SUBMITTED ON A COMPACT DISC"

Not Applicable.

BACKGROUND OF THE INVENTION

(1) Field of the Invention

The present invention relates to a process for producing one or more substituted iminoamines, in particular β-unsaturated β-iminoamines, in a single reaction comprising reacting one or more primary amines, alkynes, and isonitriles in the presence of a transition metal catalytic complex, preferably a titanium metal catalytic complex such as (N,N-di(pyrrolyl-α-methyl)-N-methylamine)titanium (Ti(NMe$_2$)$_2$(dpma)), under reaction conditions effective for 3-component coupling of the primary amines, alkynes, and isonitriles to produce one or more of the substituted iminoamines.

(2) Description of Related Art

One of the goals of methodology development in organic chemistry is to maximize the molecular complexity of the products which can be obtained in a single synthetic step (See Corey and Cheng, In *The Logic of Chemical Synthesis*, John Wiley & Sons; New York, (1995)). Coupling simple molecules in a predictable fashion is one means of achieving this goal, and the potential utility of the reaction is greatly increased if three or more molecules can be combined in a single synthetic step. For a brief overview of combinatorial chemistry see Beck-Sickinger and Weber, In *Combinatorial Strategies in Biology and Chemistry*, John Wiley & Sons; West Sussex, England, (2000). For recent articles on diversity-oriented synthesis see Schrieber, Science 287: 1964–1969 (2000); Spring et al., J. Am. Chem. Soc. 124: 1354–1363 (2002); Ding et al., J. Am. Chem. Soc. 124: 1594–1596 (2002); and Hsieh-Wilson et al., Acc. Chem. Res. 29: 164–170 (1996).

Recently, there has been considerable interest in intermolecular hydroamination of alkynes by primary amines using catalysts incorporating rhodium (Hartung et al., J. Org. Chem. 66: 6339–6343 (2001)), palladium (Kadota et al., J. Org. Chem. 64: 4570–4571 (1999); Yamamoto and Radhakrishnan, Chem. Soc. Rev. 28: 199–207 (1999)), ruthenium (Tokunaga et al., Chem. Int. Ed. 38: 3222–3225 (1999)), lanthanides Li and Marks, J. Am. Chem. Soc. 120: 1757–1771 (1998); Li and Marks, Organometallics 15: 3770–3772 (1996)), actinides (Straub et al., Organometallics 20: 5017–5035 (2001); Haskel et al., Organometallics 15: 3773–3775 (1996); Straub et al., J. Chem. Soc. Dalton Trans. 2541–2546 (1996)), and titanium (Johnson and Bergman, J. Am. Chem. Soc. 123: 2923–2924 (2001); Siebeneicher and Doye, J. Prakt. Chem. Chem. Ztg. 341: 102–106 (2000); Haak et al., Angew. Chem. Int. Ed. 38: 3389–3391 (1999); Bytschkov and Doye, Eur. J. Org. Chem. 4411–4418 (2001); Shi et al., Organometallics 21: 3967–3969 (2001); Ong et al., Organometallics 21: 2839–2841 (2002); Ackermann and Bergman, Org. Lett. 4: 1475–1478 (2002); Doye and Sibeneicher, Eur. J. Org. Chem. 1231–1220 (2002); Heutling and Doye, J. Org. Chem. 67: 1961–1964 (2002); and Haak et al., Eur. J. Org. Chem. 457–463 (2002)). Of particular interest has been the hydroamination of alkynes by primary amines using catalysts incorporating titanium. The titanium-catalyzed hydroamination reactions are often rapid, regioselective, and utilize inexpensive catalysts. More recently, the scope of titanium catalysis was expanded to produce products outside of imines using a variety of titanium catalysts for 1,1-disubstitued-hydrazine hydroamination of alkynes, which generates hydrazones and substituted indoles (Cao et al., Org. Lett. 4: 2853–2866 (2002)(web published on Jul. 26, 2002).

A single-step process for the coupling of three simple molecules via transition metal catalysis such as titanium catalysis to produce highly substituted iminoamines would be particularly desirable because such a process would provide a rapid and inexpensive means for producing useful iminoamine-based pharmaceutical chemicals. The process would also enable large libraries of iminoamine-based products to be constructed from relatively few starting materials which can be screened for useful pharmaceutical chemicals. The present invention provides a process for coupling three molecules to produce highly substituted iminoamines in a single step.

SUMMARY OF THE INVENTION

The present invention provides a process for producing one or more substituted iminoamines, in particular β-unsaturated β-iminoamines, in a single reaction comprising reacting one or more primary amines, alkynes, and isonitriles in the presence of a transition metal catalytic complex, preferably a titanium metal catalytic complex such as (N,N-di(pyrrolyl-α-methyl)-N-methylamine)titanium (Ti(NMe$_2$)$_2$(dpma)), under reaction conditions effective for 3-component coupling of the primary amines, alkynes, and isonitriles to produce one or more of the substituted iminoamines.

Therefore, the present invention provides a process for producing a substituted iminoamine which comprises reacting a primary amine, an alkyne, and an isonitrile in the presence of a catalytic complex comprising a transition metal and a ligand under reaction conditions effective for coupling the nitrogen of the primary amine to a first carbon of the triple carbon-carbon bond of the alkyne and coupling the nitrile carbon of the isonitrile to the second carbon of the triple carbon-carbon bond of the alkyne to produce the substituted iminoamine.

The present invention further provides a process for producing a substituted α,β-unsaturated β-iminoamine which comprises reacting a primary amine, an alkyne, and an isonitrile in the presence of a catalytic complex comprising a transition metal and a ligand under reaction conditions effective for coupling the nitrogen of the primary amine to a first carbon of the triple carbon-carbon bond of the alkyne and coupling nitrile carbon of the isonitrile to the second carbon of the triple carbon-carbon bond of the alkyne to produce the substituted α,β-unsaturated β-iminoamine.

The present invention further provides a process for producing a library of substituted iminoamines which comprises reacting one or more primary amines, one or more alkynes, and one or more isonitriles in the presence of a catalytic complex comprising a transition metal and a ligand under reaction conditions effective for coupling the nitrogen of the primary amine to a first carbon of the triple carbon-carbon bond of the alkyne and coupling nitrile carbon of the isonitrile to the second carbon of the triple carbon-carbon bond of the alkyne to produce the library of substituted iminoamines.

In any one of the above processes, the primary amine is selected from the group consisting of aryl amines, cyclic amines, alkylamines, substituted aryl amines, substituted cyclic amines, substituted alkylamines, and combinations thereof; the alkyne is selected from the group of consisting of terminal alkynes, internal alkynes, substituted terminal alkynes, substituted internal alkynes, and combinations thereof; and, the isonitrile is selected from the group consisting of alkyl isonitriles, aryl nitrites, substituted alkyl isonitriles, substituted aryl nitrites, and combinations thereof.

In a preferred embodiment of any one of the above processes, the transition metal comprising the catalytic complex is selected from the group consisting of titanium, zirconium, hafnium, and unnilquadium, most preferably, titanium.

In a preferred embodiment of any one of the above processes, the ligand comprising the catalytic complex is selected from the group consisting of cyclopentadienyl, thiolate, pyrrolyl, amido, guandininate, and derivatives thereof. Preferably, the ligand is a chelating pyrrolyl-based ligand selected from the group consisting of N,N-di(pyrrolyl-α-methyl)-N-methylamine (dpma), 5,5-dimethyl-dipyrrolylmethane) (dmpm), 5,5-dipropyl-dipyrrolylmethane (dppm), 5-methyl-5-ethylene-bicyclo[2.1.1]hept-2-ene-dipyrrolylmethane (mnpm), and derivatives thereof.

In a preferred embodiment of any one of the above processes, the catalytic complex is selected from the group consisting of bis(dimethylamido)(N,N-di(pyrrolyl-α-methyl)-N-methylamine)titanium (Ti(NMe$_2$)$_2$(dpma)), (bis(dimethylamido)(5,5-dipropyl-dipyrrolylmethane)titanium (Ti(NMe$_2$)$_2$(dppm)), bis(dimethylamido)(5,5-dimethyl-dipyrrolylmethane)titanium (Ti(NMe$_2$)$_2$(dmpm)), bis(dimethylamido) 5methyl-5-ethylene-bicyclo[2.1.1]hept-2-ene-dipyrrolylmethane (Ti(NMe$_2$)$_2$(mnpm)), and derivatives thereof.

In a further embodiment of any one of the above processes, the catalytic complex is anchored to a surface of a substrate, particularly, a substrate which is glass or a polymer. Examples of suitable substrates include, but are not limited to, a substrate is selected from the group consisting of norbornene, polystyrene, and derivatives thereof. Preferably, catalytic complex anchored to the substrate is selected from the group consisting of bis(dimethylamido)(N,N-di(pyrrolyl-α-methyl)-N-methylamine)titanium (Ti(NMe$_2$)$_2$(dpma)), (bis(dimethylamido)(5,5-dipropyl-dipyrrolylmethane)titanium (Ti(NMe$_2$)$_2$(dppm)), bis(dimethylamido)(5,5-dimethyl-dipyrrolylmethane)titanium (Ti(NMe$_2$)$_2$(dmpm)), bis(dimethylamido) 5-methyl-5-ethylene-bicyclo[2.1.1]hept-2-ene-dipyrrolylmethane (Ti(NMe$_2$)$_2$(mnpm)), and derivatives thereof.

In a further embodiment, the present invention provides a process for producing a substituted α,β-unsaturated β-iminoamine which comprises reacting a primary amine, an alkyne, and an isonitrile in the presence of a catalytic complex comprising a transition metal and a ligand selected from the group consisting of cyclopentadienyl, thiolate, pyrrolyl, amido, guandininate, and derivatives thereof under reaction conditions effective for coupling the nitrogen of the primary amine to a first carbon of the triple carbon-carbon bond of the alkyne and coupling nitrile carbon of the isonitrile to the second carbon of the triple carbon-carbon bond of the alkyne to produce the substituted α,β-unsaturated β-iminoamine.

In the above process, the primary amine is selected from the group consisting of aryl amines, cyclic amines, alkylamines, substituted aryl amines, substituted cyclic amines, substituted alkylamines, and combinations thereof; the alkyne is selected from the group of consisting of terminal alkynes, internal alkynes, substituted terminal alkynes, substituted internal alkynes, and combinations thereof; and, the isonitrile is selected from the group consisting of alkyl isonitriles, aryl nitrites, substituted alkyl isonitriles, substituted aryl nitrites, and combinations thereof.

In a preferred embodiment of the above process, the transition metal comprising the catalytic complex is selected from the group consisting of titanium, zirconium, hafnium, and unnilquadium, most preferably, titanium.

In a preferred embodiment of the above process, the ligand comprising the catalytic complex is a chelating pyrrolyl-based ligand selected from the group consisting of N,N-di(pyrrolyl-α-methyl)-N-methylamine (dpma), 5,5-dimethyl-dipyrrolylmethane) (dmpm), 5,5-dipropyl-dipyrrolylmethane (dppm), 5-methyl-5-ethylene-bicyclo[2.1.1]hept-2-ene-dipyrrolylmethane (mnpm), and derivatives thereof.

In a preferred embodiment of the above process, the catalytic complex is selected from the group consisting of bis(dimethylamido)(N,N-di(pyrrolyl-α-methyl)-N-methylamine)titanium (Ti(NMe$_2$)$_2$(dpma)), (bis(dimethylamido)(5,5-dipropyl-dipyrrolylmethane)titanium (Ti(NMe$_2$)$_2$(dppm)), bis(dimethylamido)(5,5-dimethyl-dipyrrolylmethane)titanium (Ti(NMe$_2$)$_2$(dmpm)), bis(dimethylamido) 5-methyl-5-ethylene-bicyclo[2.1.1]hept-2-ene-dipyrrolylmethane (Ti(NMe$_2$)$_2$(mnpm)), and derivatives thereof.

In a further embodiment of the above process, the catalytic complex is anchored to a surface of a substrate, particularly, a substrate which is glass or a polymer. Examples of suitable substrates include, but are not limited to, a substrate is selected from the group consisting of norbornene, polystyrene, and derivatives thereof. Preferably, catalytic complex anchored to the substrate is selected from the group consisting of bis(dimethylamido)(N,N-di(pyrrolyl-α-methyl)-N-methylamine)titanium (Ti(NMe$_2$)$_2$(dpma)), (bis(dimethylamido)(5,5-dipropyl-dipyrrolylmethane)titanium (Ti(NMe$_2$)$_2$(dppm)), bis(dimethylamido)(5,5-dimethyl-dipyrrolylmethane)titanium (Ti(NMe$_2$)$_2$(dmpm)), bis(dimethylamido)(5,5-dimethyl-dipyrrolylmethane)titanium (Ti(NMe$_2$)$_2$(mnpm)), and derivatives thereof.

In further embodiment, the present invention provides a process for producing a substituted α,β-unsaturated β-iminoamine which comprises reacting a primary amine, an alkyne, and an isonitrile in the presence of a catalytic complex comprising a transition metal and a ligand anchored to the surface of a substrate under reaction conditions effective for coupling the nitrogen of the primary amine to a first carbon of the triple carbon-carbon bond of the alkyne and coupling nitrile carbon of the isonitrile to the second carbon of the triple carbon-carbon bond of the alkyne to produce the substituted α,β-unsaturated β-iminoamine.

In the above process, the primary amine is selected from the group consisting of aryl amines, cyclic amines, alkylamines, substituted aryl amines, substituted cyclic amines, substituted alkylamines, and combinations thereof; the alkyne is selected from the group of consisting of terminal alkynes, internal alkynes, substituted terminal alkynes, substituted internal alkynes, and combinations thereof; and, the isonitrile is selected from the group consisting of alkyl isonitriles, aryl nitrites, substituted alkyl isonitriles, substituted aryl nitrites, and combinations thereof.

In a preferred embodiment of the above process, the transition metal comprising the catalytic complex is selected from the group consisting of titanium, zirconium, hafnium, and unnilquadium, most preferably, titanium.

In a preferred embodiment of the above process, the ligand comprising the catalytic complex is selected from the group consisting of cyclopentadienyl, thiolate, pyrrolyl, amido, guandininate, and derivatives thereof. Preferably, the ligand is a chelating pyrrolyl-based ligand selected from the group consisting of N,N-di(pyrrolyl-α-methyl)-N-methylamine (dpma), 5,5-dimethyl-dipyrrolylmethane) (dmpm), 5,5-dipropyl-dipyrrolylmethane (dppm), 5-methyl-5-ethylene-bicyclo[2.1.1]hept-2-ene-dipyrrolylmethane (mnpm), and derivatives thereof.

In a preferred embodiment of the above process, the catalytic complex is selected from the group consisting of bis(dimethylamido)(N,N-di(pyrrolyl-α-methyl)-N-methylamine)titanium (Ti(NMe$_2$)$_2$(dpma)), (bis (dimethylamido)(5,5-dipropyl-dipyrrolylmethane)titanium (Ti(NMe$_2$)$_2$(dppm)), bis(dimethylamido)(5,5-dimethyl-dipyrrolylmethane)titanium (Ti(NMe$_2$)$_2$(dmpm)), bis (dimethylamido) 5-methyl-5-ethylene-bicyclo[2.1.1]hept-2-ene-dipyrrolylmethane (Ti(NMe$_2$)$_2$(mnpm)), and derivatives thereof.

In a further embodiment of the above process, the catalytic complex is anchored to a surface of a substrate selected from the group consisting of norbornene, polystyrene, and derivatives thereof. Preferably, catalytic complex anchored to the substrate is selected from the group consisting of bis(dimethylamido)(N,N-di(pyrrolyl-α-methyl)-N-methylamine)titanium (Ti(NMe$_2$)$_2$(dpma)), (bis (dimethylamido)(5,5-dipropyl-dipyrrolylmethane)titanium (Ti(NMe$_2$)$_2$ (dppm)), bis(dimethylamido)(5,5-dimethyl-dipyrrolylmethane)titanium (Ti(NMe$_2$)$_2$ (dmpm)), bis (dimethylamido) 5-methyl-5-ethylene-bicyclo[2.1.1]hept-2-ene-dipyrrolylmethane (Ti(NMe$_2$)$_2$(mnpm)), and derivatives thereof.

The present invention further provides a compound which is (bis(dimethylamido)(5,5-dipropyl-dipyrrolylmethane) titanium (Ti(NMe$_2$)$_2$ (dppm)) or bis(dimethylamido) 5-methyl-5-ethylene-bicyclo[2.1.1]hept-2-ene-dipyrrolylmethane (Ti(NMe$_2$)$_2$(mnpm)).

The present invention further provides a compound selected from the group consisting of

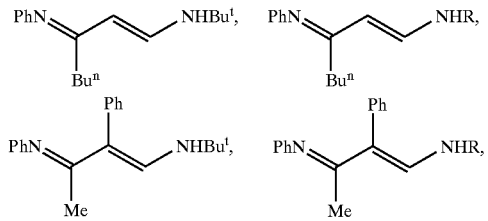

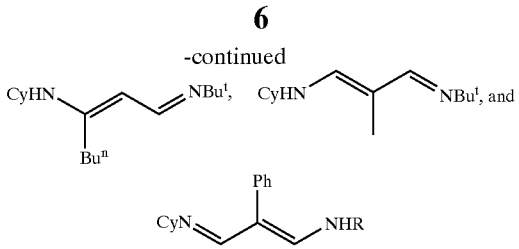

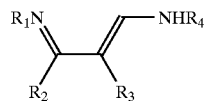

wherein Ph is phenyl, Me is methyl, Cy is cyclohexyl, Bu$^t$ is t-butyl, and Bu$^n$ is n-butyl.

The present invention further provides a substituted iminoamine which has the formula $$R_1N \diagup\!\!\!\diagdown NHR_4$$
$$\phantom{R_1N}R_2\phantom{\diagup}R_3$$

wherein each R is independently selected from the group consisting of hydrogen, methyl, alkyl, cycloalky, aryl, alkenyl, arylalkyl, alkylaryl, arylalkenyl, alkenylaryl linear or branched, combinations thereof, and substituted derivatives thereof.

OBJECTS

It is an object of the present invention to provide a transition metal-catalyzed process for producing substituted iminoamine compounds.

It is a further object of the present invention to provide a transition metal-catalyzed process for coupling three reactants to produce the substituted iminoamine compounds It is an object further still of the present invention to provide a transition metal-catalyzed process for coupling three reactants to produce α,β-unsaturated β-iminoamine derivatives.

It is an object further still of the present invention to provide a transition metal-catalyzed process for coupling three reactants to produce diimino-1,3-propandione derivatives.

These and other objects of the present invention will become increasingly apparent with reference to the following drawings and preferred embodiments.

DETAILED DESCRIPTION OF THE INVENTION

All patents, patent applications, government publications, government regulations, and literature references cited in this specification are hereby incorporated herein by reference in their entirety. In case of conflict, the present description, including definitions, will control.

The present invention has provided a solution to the problem of providing a general and efficient process for maximizing the molecular products that can be obtained in a single synthetic step. It has been discovered that transition metal catalysis, titanium catalysis in particular, can be used in a process to couple one or more primary amine, isonitriles, and alkyne reactants to form highly substituted iminoamine products, which are substituted α,β-unsaturated β-iminoamines or diimino-1,3-propandione derivatives. Thus, the process provides for the synthesis of substituted iminoamine products with the general structure of

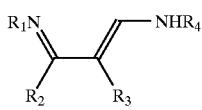

wherein each R is independently selected from the group consisting of hydrogen, methyl, alkyl, cycloalkyl, aryl, alkenyl, arylalkyl, alkylaryl, arylalkenyl, alkenylaryl linear or branched, combinations thereof, and substituted derivatives thereof.

The reaction is illustrated in Scheme 1 wherein each R of the primary amine, alkyne, and isonitrile reactants is as above and the solvent is any solvent which does not interfere with formation of the substituted iminoamine.

Scheme 1

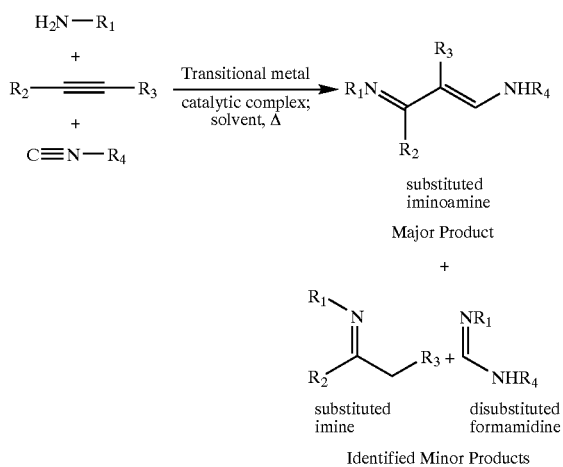

As shown in Scheme 1, the process couples one or more primary amine, alkyne, and isonitrile reactants in the presence of a transition metal catalytic complex to produce one or more iminoamines as the major product. The preferred primary amine reactants include, but are not limited to, substituted or unsubstituted alkyl amines, aryl amines (including heteroaromatic, polyaromatic, and heteropolyaromatic hydrocarbon amines), cyclic amines (including heterocyclic, polycyclic, and heteropolycyclic amines), or combinations thereof. The preferred alkynes include, but are not limited to, substituted and unsubstituted terminal alkynes, internal alkynes, or combinations thereof (including cyclic, heterocyclic, polycyclic, and heteropolycyclic alkynes). The preferred isonitriles include, but are not limited to, substituted or unsubstituted alkyl isonitriles, aryl isonitriles (including heteroaromatic, polyaromatic, and heteropolyaromatic hydrocarbon isonitriles), cyclic isonitriles (including heterocyclic, polycyclic, and heteropolycyclic isonitriles) and combinations thereof. The term "substituted" when referring to the primary amines, alkynes, and isonitriles means that the R groups of the primary amines, alkynes, and isonitriles as shown in Scheme 1 include N, O, Cl, Br, B, and the like. When referring to the iminoamine product, the term "substituted" refers to the iminoamine as shown above and in Scheme 1. Preferably, the reactants are mixed together before adding to the solvent containing the catalytic complex or mixed together in the solvent before adding the catalytic complex.

The identified minor products (by-products) of the process include disubstituted formamidine produced from the reaction of the isonitrile with the primary amine and substituted imine produced by simple alkyne hydroamination. The production of disubstituted formamidine can be catalyzed by several metal catalytic complexes (For example, see Davis and Yelland, J. Am. Chem. Soc. 59: 1998–1999 (1937); Saegusa et al., J. Org. Chem. 36: 2876–2880 (1971); and Bestchart and Hegedus, J. Am. Chem. Soc. 114: 5010–5017 (1992)). In general, the disubstituted formamidine is produced in yields less than 15% and the substituted imine is produced in only trace amounts.

The transition metal comprising the catalytic complex is coupled to a ligand. Preferably, the transition metal is a Group-4 transition metal such as titanium, zirconium, hafnium, unnilquadium, or the like. Most preferably the transition metal is titanium. The transition metal can be coupled to a ligand such as cyclopentadienyl, thiolate, pyrrolyl, amido, guandininate, and derivatives thereof. A preferred ligand is a chelating pyrrolyl-based ligand.

In a preferred embodiment, the catalytic complex is a titanium catalytic complex which comprises a chelating pyrrolyl-based ligand. Examples of chelating pyrrolyl-based ligands include, but are not limited to, of N,N-di(pyrrolyl-α-methyl)-N-methylamine (dpma), 5,5-dimethyl-dipyrrolylmethane (dmpm), 5,5-dipropyl-dipyrrolylmethane (dppm), 5-methyl-5-ethylene-bicyclo [2.1.1]hept-2-ene-dipyrrolylmethane (mnpm), and derivatives thereof. Chelation allows the synthesis of stable catalytic complexes with an $\eta^1$-coordination of the pyrrolyl substituents on the titanium as opposed to an $\eta^5$-coordination. The catalysts produced using chelating pyrrolyl-based ligands have high Lewis acidity. In a most preferred embodiment, the titanium catalytic complex is bis(dimethylamido)(N,N-di(pyrrolyl-α-methyl)-N-methylamine)titanium (Ti(NMe$_2$)$_2$(dpma)), (bis (dimethylamido)(5,5-dipropyl-dipyrrolylmethane)titanium (Ti(NMe$_2$)$_2$(dppm)), bis(dimethylamido)(5,5-dimethyl-dipyrrolylmethane)titanium (Ti(NMe$_2$)$_2$(dmpm)), bis (dimethylamido) 5-methyl-5-ethylene-bicyclo[2.1.1]hept-2-ene-dipyrrolylmethane (Ti(NMe$_2$)$_2$(mnpm)), and derivatives thereof. The structure of Ti(NMe$_2$)$_2$(dpma) was reported by Harris et al. in Inorg. Chem. 40: 1987–1988 (2001) and has the structure shown below.

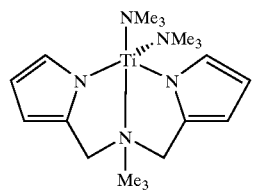

Examples of other catalytic complexes include, but are not limited to, cyclopentadienyltitanium-imido complexes and zirconium bisamides such as CpTi=NR(NHR) and Cp$_2$Zr (NHR)$_2$, respectively, wherein Cp is cyclopentadienyl and R is 2,6-Me$_2$C$_6$H$_3$ or methyl, alkyl, aryl, amide, or derivatives thereof (Straub and Bergman, Angew. Chem. Int. Ed. 40: 4632–4635 (2001); Walsh et al. J. Am. Chem. Soc. 114: 1708–1719 (1992)); enantiopure zirconocene imido complexes such as (ebthi)(L)Zr=NR wherein ebthi is bis (tetrahydroindenyl)ethane, L is tetrahydrofuran, and R is methyl, alkyl, aryl, amide, or derivatives thereof (Sweeney et al., Agnew. Chem. Int. Ed. 39: 2339–2343 (2000)); base-free titanocene imido complexes such as Cp*$_2$Ti=NPh wherein Cp* is pentamethylcyclopentadienyl and Ph is phenyl (Polse et al., J. Am. Chem. Soc. 120: 13405–13414

(1998)); imidozirconium complexes such as Cp$_2$Zr=NAr (Baranger et al., J. Am. Chem. Soc. 115: 2753–2763 (1993)); dimethyltitanocene complexes such as Cp$_2$TiMe$_2$ (Pohlki and Doye, Agnew. Chem. Int. Ed. 40: 2305–2308 (2001); Ti(Me$_2$)$_4$ (Shi et al., Organometal. 20: 3967–3969 (2001); guanidinate-supported metal imido complexes such as {(Me$_2$N)C(N$^i$Pr)$_2$}$_2$TiNAr and {(Me$_2$N)C(N$^i$Pr)$_2$}$_2$ZrNAr (Ong et al., Organometal. 21-2839–2841 (2002)); tetrakisamido titanium complexes (Ackermann and Bergman, Org. Letts. 4: 1475–1478 (2002); and, titanocene alkyne complexes such as Cp$_2$Ti($\eta^2$-Me$_3$SiC≡CSiMe$_3$) and CP$_2$Ti($\eta^2$-Me$_3$SiC≡CSiPh) (Tillack et al., Agnew. Chem. Int. Ed. 41: 2541–2543 (2002).

While the solvent can be any solvent which does not interfere with the 3-component coupling process, a preferred solvent is an aprotic solvent including, but not limited to, aromatic hydrocarbons such as toluene and xylene, chlorinated aromatic hydrocarbons such as dichlorobenzene, and ethers such as tetrahydrofuran. The amount of solvent can be any amount but preferably an amount sufficient to solubilize, at least in part, the reactants. A suitable quantity of solvent ranges from about 1 to about 100 grams of solvent per gram of reactants. Other quantities of solvent may also be suitable depending on the particular reaction conditions and by one skilled in the art.

The 3-component coupling process can be performed in a vessel open to air or in a vessel in which the air has been removed. In cases where the air is removed, the reaction mixture can be purged of air with a non-reactive gas such as nitrogen, helium, or argon. Thus, the 3-component coupling process can be performed under anaerobic conditions. The 3-component coupling process conditions can include any operable conditions which yield the desired coupled products. For example, the preferred temperature can be a temperature from ambient (about 22° C.) to about 200° C., preferably at about 100° C. The 3-component coupling process can be performed at atmospheric pressure or at a pressure lesser or greater than atmospheric pressure. The 3-component coupling process is performed for a time sufficient to convert a substantial amount of the reactants into the desired coupled product. In general, the reaction time for producing a desired coupled product ranges from about 24 to 48 hours. The coupled products produced in a 3-component coupling reaction can include at least 50% or greater of one regioisomer.

In a preferred 3-component coupling process, the catalytic complex is selected from the group consisting of Ti(NMe$_2$)$_2$ (dpma), Ti(NMe$_2$)$_2$(dmpm), Ti(NMe$_2$)$_2$(dppm), and Ti(NMe$_2$)$_2$(mnpm). Preferably, the catalytic complex is provided in the reaction at about 10 mol % in an organic solvent which preferably is toluene, and the reaction is performed at about 100° C. The preferred 3-component coupling process is illustrated in Examples 2 to 10.

The 3-component coupling process can be performed in any conventional reactor designed for catalytic processes. Continuous, semi-continuous, and batch reactors can be used. If the catalyst is substantially dissolved in the reaction mixture as in homogeneous processes, then batch reactors, including stirred tank and pressurized autoclaves can be used. In a typical reaction, the reactants and catalyst are mixed in a solvent and the reaction performed in a batch reactor at a temperature and pressure effective for 3-component coupling.

Catalytic complexes containing dipyrrolylmethane ligands can be tethered to surfaces such as norbornene, polystyrene, glass, or other polymers in several different ways. If the catalyst is anchored to a support and is substantially in a heterogeneous phase, then fixed-bed and fluidized bed reactors can be used. For example, a titanium-dipyrrolylmethane derivative with a norbornene tethered to the 5-position is co-polymerized with norbornene to give a copolymer with the catalytic complex attached.

The 3-component coupling process can include one each of a particular substituted or unsubstituted primary amine, alkyne, and isonitrile to produce a particular species of coupled product. Alternatively, the 3-component coupling process can include any number of substituted or unsubstituted primary amines, any number of substituted or unsubstituted alkynes, and any number of substituted or unsubstituted isonitriles to produce a library containing a plurality of coupled products.

The coupled products can be isolated by conventional means known to those skilled in the art, including for example, chromatography, distillation, crystallization, and sublimation. The yield of major and minor products will depend on the particular catalytic complexes, reactants, solvent, and process conditions used. Typically, the product yields are in terms of mole percentage of product recovered.

The inexpensive, readily-available or synthesizable transition metal catalytic complexes, such as the titanium catalytic complexes, catalyze a 3-component coupling of an isonitrile, an amine, and alkyne. The reaction products produced are often diimino-1,3-propanedione derivatives. Highly unsymmetrical compounds are produced, often with high regioselectivity. The products are also ligands which are often used for both early and late transition metals. Complexes of these ligands can be olefin polymerization catalysts. The products are also useful as starting materials for a variety of common organic transformations which can lead to production of important compounds for pharmaceutical or other applications. Because many of the diimino-1, 3-propanedione derivatives can be prepared from relatively few starting materials using combinatorial methods, the titanium catalysts and process of the present invention are of particular interest to those interested in olefin polymerization and pharmaceuticals.

The 3-component coupling process of the present invention provides several advantages over the processes of the prior art. First, the reaction couples three simple starting materials in a single step. The advantage is that using combinatorial methodologies, relatively few starting materials can be combined to produce a large library of compounds for testing in specific applications.

Second, the coupled products are highly unsymmetrical and a single reaction often yields only a single isomer of coupled product. This advantage avoids the time and expense of purifying various isomers of a particular coupled product.

Third, the 3-component coupling process enables coupled products to be produced which are inaccessible using prior art processes. For example, diimines of 2-mesityl-2,4-pentandione cannot be prepared using prior art condensation methods. However, regiochemical data indicates that functional derivatives of those diimines should be accessible using the 3-component coupling process disclosed herein.

The following examples are intended to promote a further understanding of the present invention.

EXAMPLE 1

This example shows the synthesis of the titanium catalytic complex, titanium pyrroyl complex Ti(NMe$_2$)$_2$(dpma), wherein dpma is N,N-di(pyrrolyl-α-methyl)-N-methylamine. The H$_2$dpma ligand was prepared in a single, high-yielding step (70–80%) by Mannich reaction between pyrrole, methylamine hydrochloride, and formaldehyde in a modification of the process in Raines and Kovacs, J. Heterocyclic Chem. 7: 233 (1970) as described in Harris et al., Inorg. Chem. 40: 1987–1988 (2001). Synthesis of the Ti(NMe$_2$)$_2$(dpma) is shown in Equation 1.

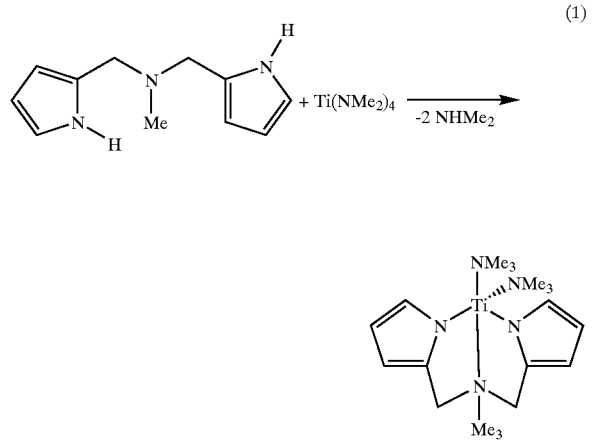

(1)

The Ti(NMe$_2$)$_2$(dpma) was prepared in near quantitative yield by treatment of commercially available Ti(NMe$_2$)$_4$ with the H$_2$dpma as described below.

Briefly, Ti(NMe$_2$)$_4$ (1.098 g, 3.1704 mmol) was dissolved in Et$_2$O (10 mL) and chilled to −35° C. A 5 mL solution of H$_2$dpma (0.600 g, 3.1704 mmol) in Et$_2$O was added dropwise. After 30 minutes, the volatiles were removed and a yellow powder remained. X-ray quality crystals were obtained from pentane/Et$_2$O at −35° C. in 97.1% yield (0.955 g). $^1$H NMR (300 MHz, CDCl$_3$): δ6.89(m, 2H), 6.07(m, 2H), 5.90(m, 2H) 4.03 (d, J=14 Hz, 2H), 3.75 (d, J=14 Hz, 2H), 3.30 (s, 12H), 2.49 (s, 3H). $^{13}$C NMR (CDCl$_3$): δ137.40, 126.64, 107.62, 102.54, 57.90, 47.18, 45.90, 42.82. MS (70 eV): m/z(%) 323.4(0.18)[M$^+$]. Elemental Anal. Calc. For C$_{15}$H$_{25}$N$_5$Ti: C, 55.73; H, 7.80; N, 21.66. Found: C, 55.64; H, 7.52; N, 21.38.

To avoid isolation of the air-sensitive complex, Ti(NMe$_2$)$_2$(dpma) can be readily produced in situ with comparable catalytic activity. Ti(NMe$_2$)$_2$(dpma) has a relatively broad scope and is applicable for hydroamination of terminal and internal alkynes by alkyl and aryl amines (Cao et al., Organometallics 20: 5011–5013 (2001)). A competing reaction leading to oligomerization of terminal alkynes is only observed when the alkyne has appreciable acidity, for example, phenylacetylene.

EXAMPLE 2

This example shows that Ti(NMe$_2$)$_2$(dpma) catalyzes the 3-component coupling of isonitriles, primary amines, and alkynes to produce highly substituted iminoamines in a single step reaction. The generalized reaction was as shown in Scheme 1 wherein the solvent was toluene.

The major products for the majority of the substrates used were due to 3-component coupling. Two by-products that had been identified from the reaction mixtures were N,N'-disubstituted-formamidine from the reaction of isonitrile with the primary amine and substituted imines. The disubstituted formamidines were the most common by-product and were found in the largest quantities for reactions involving internal alkynes. In some cases, the substituted imines from simple alkyne hydroamination were also observed. However, with the substrates investigated so far, the imine by-product was produced in only trace quantities as analyzed by GC-FID of crude reaction mixtures. The desired product was isolated by chromatography on silica gel.

Some representative examples of 3-component coupling reactions are given in Table 1. The listing of substrates in Table 1 includes alkyl amines, aryl amines, terminal alkynes, internal alkynes, alkyl isonitriles, and aryl nitriles. In a couple of cases, the formamidine by-products were produced in sufficient quantities to allow isolation (by-product 1a), and in those cases the yields for the formamidine by-products are provided. Other reactions had smaller quantities of formamidine observable by GC. In most cases, 1.1 or 1.2 equivalents of isonitrile was used to compensate for formamidine production. Other by-products for the reactions were sometimes present (not shown). Because these by-products can be useful, studies are underway which are aimed at isolation and structural characterization of the by-products.

TABLE 1

| Amine | Alkyne | Isonitrile[a] | Product[b] (% yield) | By-product (% yield) |
|---|---|---|---|---|
| PhNH$_2$ | Bu$^n$—≡—H | C≡N—Bu$^t$ | PhN=C(Bu$^n$)—CH=NHBu$^t$  1 (77%) | PhN=CH—NHBu$^t$  1a (13%) |
| PhNH$_2$ | Bu$^n$—≡—H | C≡N—R | PhN=C(Bu$^n$)—CH=NHR  2 (83%) | — |

TABLE 1-continued

| Amine | Alkyne | Isonitrile[a] | Product[b] (% yield) | By-product (% yield) |
|---|---|---|---|---|
| PhNH$_2$ | Ph—≡—Me | C≡N—Bu$^t$ | PhN=C(Me)—C(Ph)=CH—NHBu$^t$<br>3 (72%) | PhN=CH—NHBu$^t$<br>1a (15%) |
| PhNH$_2$ | Ph—≡—Me | C≡N—R | PhN=C(Me)—C(Ph)=CH—NHR<br>4 (57%) | — |
| CyNH$_2$[c] | Bu$^n$—≡—H | C≡N—Bu$^t$ | CyHN—C(Bu$^n$)=CH—CH=NBu$^t$<br>5a<br><br>CyHN—CH=C(Bu$^n$)—CH=NBu$^t$<br>5b<br>(1.2:1, 66%) | — |
| CyNH$_2$[c] | Ph—≡—H | C≡N—R | CyN=CH—C(Ph)=CH—NHR<br>6 (68%) | — |

[a]R = 1,1,3,3-tetramethylbutane
[b]Reactions were carried out at 100° C. in toluene with 10 mol % Ti(NMe$_2$)$_2$(dpma). The products were isolated on multigram scales by chromatography.
[c]Cy = cyclohexyl
Reaction conditions and analyses for the products are provided in Examples 6–10.

The desired compounds were purified and isolated on multigram scales by column chromatography. The products have multiple tautomers accessible. For most of the reactions, the more stable tautomer, as determined by NMR spectroscopy, is shown. Product 5b appears to be a tautomeric mixture in solution.

With Ti(NMe$_2$)$_2$(dpma) as the catalyst, the synthesis was successful with aryl amines, alkyl amines, terminal alkynes, and internal alkynes with isonitriles bearing a quarternary alkyl group. Reactions with phenyl isonitrile and cyclohexyl isonitrile have not yielded 3-component coupling products under the same conditions. Alternative reaction conditions, catalysts, and the like, are under exploration with the substrates.

A couple of control experiments were performed which provided the following information. First, the three components did not react in the absence of the catalyst, even to form the observed by-products of the catalytic reaction. Second, treatment of isolated imine with isonitrile in the presence of the catalyst did not result in the production of the 3-component coupling product. Therefore, the reaction was not merely hydroamination followed by catalyzed reaction with an isonitrile. The isonitrile must be present during the C—N bonding forming reaction to yield the substituted α,β-unsaturated β-iminoamine products.

In light of the above, the 3-component coupling reaction most likely operates as follows. The catalysis involves the selective reaction of the isonitrile with an intermediate in the hydroamination catalysis. Schematically, the product would be produced from 1,1-insertion of the isonitrile into the metalloazacyclobutane intermediate formed on (2+2) cycloaddition of alkyne to a titanium terminal imido. For mechanistic studies on Group-4 metal catalyzed hydroamination see Straub and Bergman, Angew. Chem. Int. Ed. 40: 4632–4635 (2001); Sweeney et al., Angew. Chem. Int. Ed. 39: 2339–2343 (2000); Polse et al., J. Am. Chem. Soc. 120: 13405–13414 (1998); Baranger et al., J. Am. Chem. Soc. 115: 2753–2761 (1993); Walsh et al., J. Am. Chem. Soc. 114: 1708–1719 (1992); and, Pohlki and Doye, Angew. Chem. Int. Ed. 40: 2305–2308 (2001). A highly simplified catalytic cycle in agreement with the data herein is shown in Scheme 2.

Scheme 2

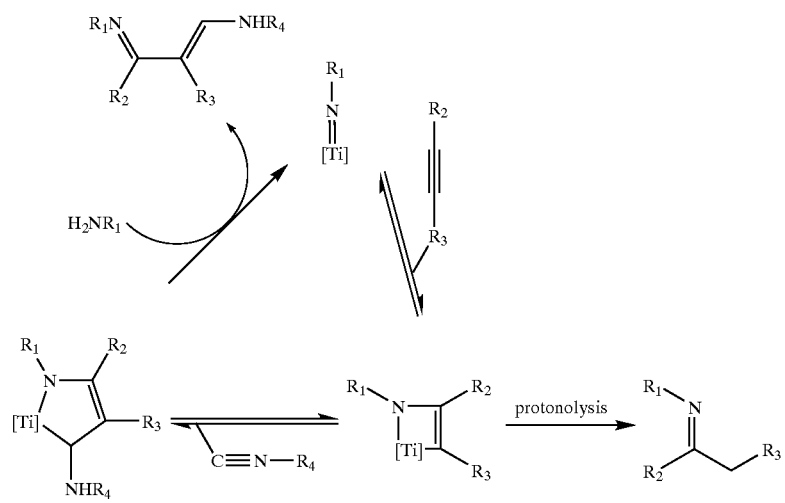

Regioselectivities in the 3-component coupling reactions using Ti(NMe$_2$)$_2$(dpma) as the catalyst have been similar to results expected from hydroamination despite the different reaction constions. For example, hydroamination of 1-hexyne by cyclohexylamine produces a 1.6:1 mixture of Markovnikov:anti-Markovnikov products. Three-component coupling between 1-hexyne, cyclohexylamine, and tert-butylisonitrile results in a 1.2:1 mixture of regioisomers (products 5a and 5b). The two isomers were separable by column chromatography. Similarly, cyclohexylamine hydroamination of phenylacetylene with Ti(NMe$_2$)$_2$ (dpma) as the catalyst produced a 1:3.5 Markovnikov:anti-Markovnikov isomer ratio (The method used to work-up and analyze hydroamination reactions in Cao et al., Organometallics 20: 5011–5013 (2001) led to a loss of anti-Markovnikov product and was incorrect regioselectivity measurements when phenylacetylene was the substrate. The correct regioselectivity is as herein). Consistent with this, the major isomer produced during the 3-product coupling has the nitrogen bearing the cyclohexyl group was observed by GC in the crude reaction mixture as a minor product but was not isolated. The ratio for the regioisomers as determined by GC/FID was 1:8.

The products generated during the process are reminiscent of β-diketimines, which in deprotonated form are common ligands for both early and late transitions metals. The titanium catalyst allows access to high unsymmetrical derivatives in a single step. For recent examples of transition metal β-diketiminate chemistry see Kakaliou et al., Inorg. Chem. 38: 5964–5977 (1999); Fekl and Goldberg, J. Am. Chem. Soc. 124: 6804–6805 (2002); Spencer et al., J. Am. Chem. Soc. 124: 2108–2109 (2002); Smith et al., J. Am. Chem. Soc. 123: 9222–9223 (2002); Dai and Warren, Chem. Commun. 1998–1999 (2001), and Bourget-Merle et al., Chem. Rev. 102: 3031–3066 (2002). In addition, 1-azabutadienes can be used in Diels-Alder reactions to form heterocycles (See Boger and Weinreb, In *Hetero Diels-Alder Methology in Organic Synthesis*, Academic Press, Inc. San Diego, Calif. (1987)). For example, α,β-unsaturated β-iminoamines react with ketenes to produce 3,4-dihydro-2-pyridones (See Brady and Shieh, J. Org. Chem. 48: 2499–2502 (1983)).

EXAMPLES 3–10

This example provides the conditions that were used for titanium-catalyzed 3-compound couplings of the reactants shown in Table 1. The scale, purification procedure, and data are provided for each product produced. Assignment of the most stable tautomer for most products was possible using standard NMR techniques. Product 5b appears to be a mixture of tautomers in the temperature range of +45 to −55° C. $^1$H and $^{13}$C NMR spectra for products 5a and 5B have been provided to demonstrate the purity of these isomers, which are also pure by TLC and GC. The procedures shown in this example are representative.

Product 1

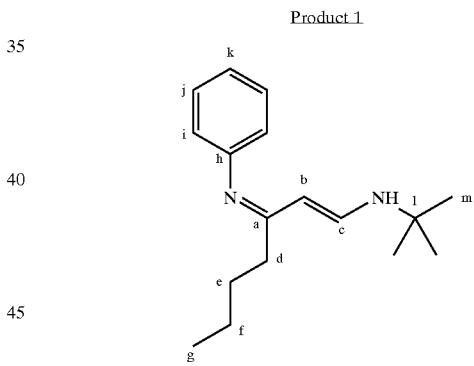

All manipulations were done in an inert atmosphere dry box under purified N$_2$. In a 40 mL pressure tube was loaded 1 mmol of Ti(NMe$_2$)$_2$(dpma) (2.0 M solution in toluene, 0.10 equiv.), aniline (1 equiv., 10 mmol, 0.911 mL), 1-hexyne (1 equiv., 10 mmol, 1.149 mL), and tert-butyl isocyanide (1 equiv., 10 mmol, 1.131 mL). The solution was diluted with toluene to 10 mL. The reaction was stirred at 100° C. for 24 hours. The solution was flushed through a pad of alumina (activated neutral) on a fritted funnel. Volatiles were removed by rotary evaporation, and distilled. Product 1 was obtained as a yellow oil (2.01 g, 7.78 mmol, 77%) by vacuum distillation (89–90° C., about 0.2 mmHg). M=258.41 g/mol, $^1$H NMR (300 MHz, CDCl$_3$): δ=10.1 (br d, 1H, NH), 7.39–7.33 (m, 2H, j), 7.14–7.04 (m, 1H, k), 6.91–6.85 (m, 3H, {c & i}), 4.82 (d, J=8 Hz, 1H, b), 2.27 (t, 2H, d), 1.61–1.50 (m, 2H, e), 1.35 (s, 9H, m), 1.29 (t, 2H, f), 0.89 (t, 3H, g). $^{13}$C NMR (CDCl$_3$): δ=170.8 (a), 151.4 (h), 142.1 (c), 128.3 (j), 121.7(k), 121.3 (i), 91.7 (b), 50.8 (d), 33.3 (e), 30.8 (1), 30.2 (m), 22.6 (f), 13.7 (g). Elemental

Product 2

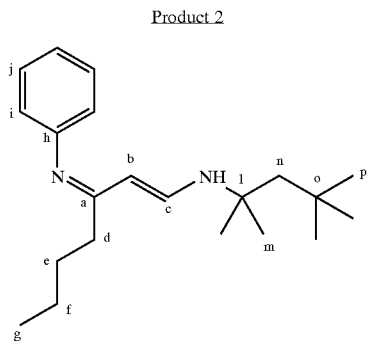

The reaction was carried out with a mixture of 1,1,3,3-tetramethylbutyl isocyanide (1.2 equiv., 12 mmol, 2.100 mL), aniline (1 equiv., 10 mmol, 0.911 mL), 1-hexyne (1 equiv., 10 mmol, 1.149 mL), and Ti(NMe$_2$)$_2$(dpma) (0.10 equiv., 2.0 M solution in toluene, 1 mmol). The mixture was heated for 48 h at 100° C. Purification was accomplished by flash chromatography on alumina. The eluant was pentane:ether (8:1) increasing to (1:1), which afforded product 2 (2.60 g, 8.27 mmol, 83%) as a yellow oil. M=314.51 g/mol, $^1$H NMR (300 MHz, 2 CDCl$_3$): δ=10.18 (br s, 1H, NH), 7.34–7.29 (m, 2H, j), 7.03 (m, 1H, k), 6.83–6.78 (m, 3H, {c & i}), 4.77 (d, J=8 Hz, 1H, b), 2.20 (t, 2H, d), 1.55 (s, 2H, n), 1.50 (m, 2H, e), 1.35 (s, 6H, m), 1.26 (m, 2H, f), 1.04 (s, 9H, p), 0.83 (t, 3H, g). $^{13}$C NMR (CDCl$_3$): δ=170.7 (a), 151.7 (h), 142.2 (c), 128.4 (j), 121.7 (k), 121.2 (i), 91.6 (b), 55.6 (n), 54.4 (l), 33.3 (d), 31.6 (o), 31.4 (p), 30.9 (e), 30.2 (m), 22.6 (f), 13.8 (g). Elemental Analysis: Calc. for C$_{21}$H$_{34}$N$_2$: C, 80.20; H, 10.90; N, 8.91. Found: C, 79.96; H, 11.21; N, 8.70. MS (EI) m/z=314 (M+).

Product 3

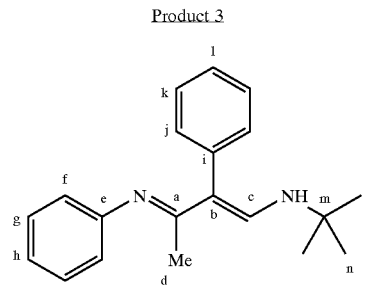

The reaction was carried out with tert-butyl isocyanide (1.2 equiv., 12 mmol, 1.357 mL), aniline (1 equiv., 10 mmol, 0.911 mL), 1-phenylpropyne (1 equiv., 10 mmol, 0.911 mL), and Ti(NMe$_2$)$_2$(dpma) (0.10 equiv., 2.0 M solution in toluene, 1 mmol). The reaction was heated for 48 hour at 100° C. Purification by flash chromatography on alumina with pentane:ether (8:1) afforded product 3 (2.10 g, 7.18 mmol, 72%) as a yellow solid. M=292.42 g/mol, Mp=90–91° C., $^1$H NMR (500 MHz, CDCl$_3$): δ=10.83 (br s, 1H, NH), 7.34–7.28 (m, 6H, {g, j, & k}), 7.26–7.18 (m, 1H, l), 7.05 (m, 1H, h), 6.96 (d, 1H, c), 6.92 (d, 2H, f), 1.84 (d, 3H, d), 1.33 (s, 9H, n). $^{13}$C NMR (CDCl$_3$): δ=166.6 (a), 151.1 (e or i), 144.1 (c), 142.7 (e or i), 130.6 (k), 128.6 (g), 128.0 (j), 125.4 (l), 122.3 (h), 121.5 (f), 107.8 (b), 51.4 (m), 30.4 (n), 20.5 (d). Elemental Analysis: Calc. for C$_{20}$H$_{24}$N$_2$: C, 82.15; H, 8.27; N, 9.58. Found: C, 82.20; H, 8.40; N, 10.11. MS (EI) m/z=292 (M+).

Product 4

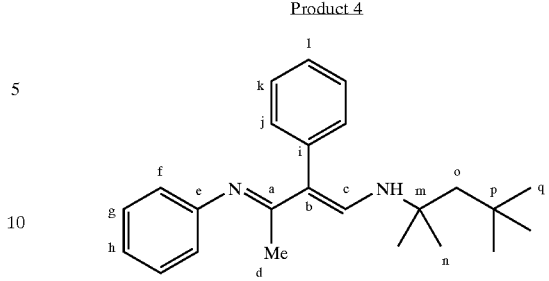

The reaction was carried out with 1,1,3,3-tetramethylbutyl isocyanide (1.2 equiv., 12 mmol, 2.100 mL), aniline (1 equiv., 10 mmol, 0.911 mL), 1-phenylpropyne (1 equiv., 10 mmol, 0.911 mL), and Ti(NMe$_2$)$_2$(dpma) (0.10 equiv., 2.0 M solution in toluene, 1 mmol). The reaction was heated for 48 hours at 100° C. Purification by flash chromatography on alumina with pentane:ether (8:1) as eluant afforded product 4 (2.00 g, 5.74 mmol, 57%) as a yellow oil. M=348.53 g/mol, $^1$H NMR (300 MHz, CDCl$_3$): δ=11.02(d, 1H, NH), 7.46–7.24 (m, 7H, {j, g, k, & l}), 7.13 (t, 1H, k), 7.05–6.90 (m, 3H, {c & f}), 1.92 (s, 3H, d), 1.67 (s, 2H, o), 1.46 (s, 6H, n), 1.14 (s, 9H, q). $^{13}$C NMR(CDCl$_3$): δ=166.5 (a), 151.4 (i or e), 143.98 (c), 142.8 (i or e), 130.6 (k), 128.6 (j or g), 127.96 (j or g), 125.3 (l), 122.1 (h), 121.3 (f), 107.6 (b), 55.6 (O), 54.7(m), 31.6 (p), 31.5 (q), 30.3 (n), 20.4 (d). Elemental Analysis: Calc. for C$_{24}$H$_{32}$N$_2$: C, 82.71; H, 9.25; N, 8.04. Found: C, 82.67; H, 9.24; N, 8.00. MS (EI) m/z=348 (M+).

Product 5a

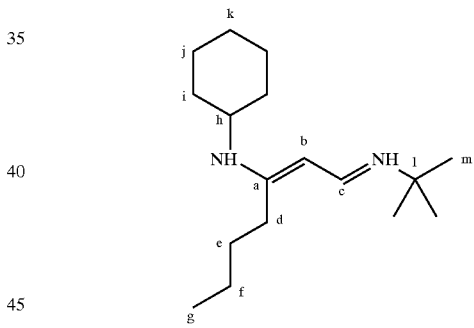

The reaction was carried out with tert-butyl isocyanide (1.1 equiv., 11 mmol, 1.240 mL), cyclohexylamine (1 equiv., 10 mmol, 1.15 mL), 1-hexyne (1 equiv., 10 mmol, 1.15 mL), and Ti(NMe$_2$)$_2$(dpma) (0.10 equiv., 2.0 M solution in toluene, 1 mmol). The vessel was heated for 24 hours at 100° C. Distillation under reduce pressure (90–92° C., about 0.2 mmHg) afforded a mixture of regioisomers. Flash chromatography on alumina (ether) gave fractions highly enriched in product 5b. Ethanol as eluant gave fractions highly enriched in product 5a. Flash chromatography of the fractions enriched with product 5a on alumina using dichloromethane:methanol (40:1) afforded the pure product (0.9545 g, 3.609 mmol), which is a colorless solid. M=264.45 g/mol, Mp=102–103° C., $^1$H NMR (300 MHz, CDCl$_3$): δ=9.33 (br d, 1H, NH), 7.43 (d, J=12 Hz, 1H, c), 5.98 (d, J=12 Hz, 1H, b), 3.33 (m, 1H, h), 2.59 (t, 2H, d), 1.76 (m, 2H, i), 1.57 (m, 2H, j), 1.52–1.34 (m, 5H, {j, i & e}), 1.34–1.08(m, 13H, {e, f, m & k}), 1.08–0.90 (m, 1H, k), 0.77 (t, 3H, g). $^{13}$C NMR (CDCl$_3$): d=170.4 (a), 153.4 (c), 88.9 (b), 53.99 (l), 53.0 (h), 32.5 (i), 31.3 (e), 30.8 (f), 29.2

Analysis: Calc. for C$_{17}$H$_{26}$N$_2$: C, 79.02; H, 10.14; N, 10.84. Found: C, 78.25; H, 9.63; N, 10.70. MS (EI) m/z=258 (M+).

(m), 24.8 (k), 24.4 (j), 21.8 (d), 13.5 (g). MS (EI) m/z=264 (M+).

Product 5b

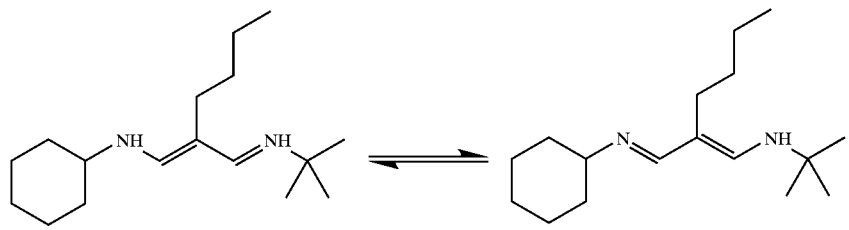

Flash chromatography on alumina using dichloromethane:methanol (40:1) of fractions enriched in product 5b removed impurities. Using methanol as eluant afforded pure 5b (0.7955 g, 3.008 mmol), which was a colorless solid. The NMR data for this molecule suggested that multiple tautomeric forms of product 5b were present. This was expected considering the electronic preference for one tautomer over another is determined by the difference between the cyclohexyl and tert-butyl groups. The NMR spectra for the tautomeric mixture with overlapping resonances were not assigned. However, the compound was greater than 90% pure by NMR, GC, and TLC. The numerical data is reported with apparent multiplicities. M=264.45 g/mol, Mp=103–104° C., $^1$H NMR (300 MHz, CDCl$_3$): δ=9.19 (br dd), 8.06 (d, J=15 Hz), 7.49 (dd, J=16 Hz), 3.28 (m), 2.62 (t), 1.84 (d), 1.81–1.00 (m), 0.77 (t). $^{13}$C NMR (CDCl$_3$): δ=159.95, 156.9, 106.9, 59.2, 55.2, 32.9, 29.7, 29.5, 24.9, 24.7, 22.2, 21.9, 14.3. MS (EI) m/z=264 (M+). For both regioisomers, the reaction yielded 1.75 g (66% total yield, 5a:5b=1.2:1) of purified product.

Product 6

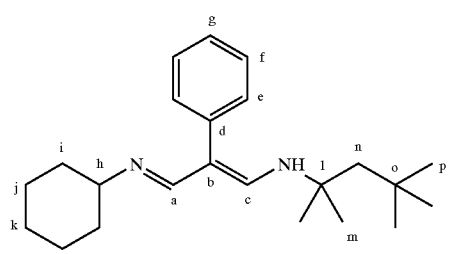

The reaction was carried out with 1,1,3,3-tetramethylbutyl isocyanide (1.1 equiv., 11 mmol, 1.925 mL), cyclohexylamine (1 equiv., 10 mmol, 1.15 mL), phenylacetylene (1 equiv., 10 mmol, 1.10 mL), and Ti(NMe$_2$)$_2$ (dpma) (0.10 equiv., 2.0 M solution in toluene, 1 mmol). The reaction was heated for 20 hours at 100° C. Flash chromatography on alumina with pentane:ether (40:1) as eluant followed by chromatography with pentane:ether (2:1) produced product 6 (2.312 g, 6.79 mmol, 68%) as a yellow oil. NMR spectroscopy is consistent with predominantly one isomer being present in CDCl$_3$ at room temperature, which has tentatively been assigned to the above structure. M=340.54 g/mol, $^1$H NMR (300 MHz, CDCl$_3$): δ=11.10 (br s, 1H, NH), 8.05 (d, J=3 Hz, 1H, c), 7.41 (d, J=3 Hz, 1H, a), 7.36–7.29 (m, 4H, {e & f}), 7.15 (tt, 1H, g), 3.11 (m, 1H, h), 1.91–1.83 (m, 4H, j), 1.65 (s, 2H, n), 1.56–1.43 (m, 4H, i), 1.43 (s, 6H, m), 1.41–1.32 (m, 2H, k), 1.07 (s, 9H, p). $^{13}$C NMR (CDCl$_3$): δ=156.3 (c), 144.5 (a), 142.0 (d), 128.3 (e), 124.9 (f), 123.7 (g), 103.6 (b), 66.2 (h), 55.97 (n), 55.6 (l), 35.2 (k), 31.7 (o), 31.5 (p), 30.3 (m), 25.8 (i), 24.6 (j).

Elemental Analysis: Calc. for C$_{23}$H$_{36}$N$_2$: C, 81.12; H, 10.65; N, 8.23. Found: C, 81.12; H, 10.98; N, 8.39. MS (EI) m/z=340 (M+).

By-Product 1a

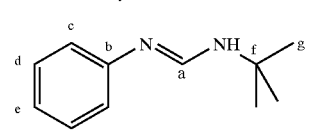

For the reactions producing products 1 and 3, a by-product of N-phenyl-N'-tert-butylformamidine was isolated (by-product 1a). This was accomplished using sublimation (80° C., about 0.2 mmHg) affording 0.2327 g (1.32 mmol, 13.2%) and 0.2556 g (1.45 mmol, 14.5%), respectively. The by-product was then isolated by chromatography as described. M=176.26 g/mol, Mp=88–89° C., $^1$H NMR (300 MHz, CDCl$_3$): δ=7.74 (s, 1H, a), 7.38–7.22 (m, 2H, d), 7.10–7.01 (m, 1H, e), 7.01–6.88 (m, 2H, c), 5.94 (br s, 1H, NH) 1.33 (s, 9H, g). $^{13}$C NMR (CDCl$_3$): δ=151.5 (b), 150.7 (a), 128.9 (d), 122.6 (e), 120.9 (c), 50.6 (f), 30.6 (g). Elemental Analysis: Calc. for C$_{11}$H$_{16}$N$_2$: C, 74.96; H, 9.15; N, 15.89. Found: C, 74.85; H, 9.28; N, 15.79. MS (EI) m/z=176 (M+).

EXAMPLE 11

This example provides a method for preparing Ti(NMe$_2$)$_2$ (dmpm) which is an effective catalyst for 3-component couplings.

In an inert atmosphere dry box under purified N$_2$, a thawing solution of 0.7590 g (4.36×10$^{-3}$ moles) H$_2$dmpm (FW 174.24) in about 10 mL ether was added to a thawing solution of 1030.0 μL Ti(NMe$_2$)$_4$ (FW 224.02 (d=0.947), 0.9754 g, 4.35×10$^{-3}$ moles) in 50 mL ether. The mixture was stirred for about two hours and then the volatiles were removed, leaving an orange-yellow solid comprising the Ti(NMe$_2$)$_2$(dmpm). The yield was 1.138 g (3.69×10$^{-3}$ moles) which was 84.8%. The formula weight of the catalyst was 308.28.

A 3-component coupling to produce compound 1 is carried out in an inert atmosphere dry box under N$_2$ as follows. In a 40 mL pressure tube is loaded 1 mmol of the catalyst (2.0 M solution in toluene, 0.10 equiv.), aniline (1 equiv., 10 mmol, 0.911 mL), 1-hexyne (1 equiv., 10 mmol, 1.149 mL), and tert-butyl isocyanide (1 equiv., 10 mmol, 1.131 mL). The solution is diluted with toluene to 10 mL. The reaction is stirred at 100° C. for 24 hours. The solution is flushed through a pad of alumina (activated neutral) on a fritted funnel. Volatiles are removed by rotary evaporation, and distilled. Product 1 is obtained as a yellow oil by vacuum distillation (89–90° C., about 0.2 mmHg).

EXAMPLE 12

This example provides a method for preparing $Ti(NMe_2)_2$ (dppm) which is an effective catalyst for 3-component couplings.

In an inert atmosphere dry box under purified $N_2$, a thawing solution of 0.2222 g ($1.00 \times 10^{-3}$ moles) $H_2$ppm (FW 174.24) in about 5 mL ether was added to a thawing solution of 255 µL $Ti(NMe_2)_4$ (FW 224.02 (d=0.947), 0.2415 g, $0.998 \times 10^{-3}$ moles) in 5 mL ether. The mixture was stirred for about two hours and then the volatiles were removed in vacuo, leaving a yellow solid which by $^1$H NMR appeared to be $Ti(NMe_2)_2$(dppm). The yield was 0.3210 g ($7.69 \times 10^{-3}$ moles) which was 77.1%. The formula weight of the catalyst was 417.41.

A 3-component coupling to produce compound 1 is carried out in an inert atmosphere dry box under $N_2$ as follows. In a 40 mL pressure tube is loaded 1 mmol of the catalyst (2.0 M solution in toluene, 0.10 equiv.), aniline (1 equiv., 10 mmol, 0.911 mL), 1-hexyne (1 equiv., 10 mmol, 1.149 mL), and tert-butyl isocyanide (1 equiv., 10 mmol, 1.131 mL). The solution is diluted with toluene to 10 mL. The reaction is stirred at 100° C. for 24 hours. The solution is flushed through a pad of alumina (activated neutral) on a fritted funnel. Volatiles are removed by rotary evaporation, and distilled. Product 1 is obtained as a yellow oil by vacuum distillation (89–90° C., about 0.2 mmHg).

EXAMPLE 13

This example provides a method for preparing $Ti(NMe_2)_2$ (mnpm) (FW 594.8) which is an effective catalyst for 3-component couplings.

The mnpm was prepared as follows. Into a 500 ml schlenk flask was placed 15.0 g 5-(butan-3-one)-norbornylene (FW 164.26, $9.13 \times 10^{-2}$ moles), 180 mL pyrrole (FW 67.09), and a stir bar. A septum was used to cap the flask and the flask was purged with argon for about 30 minutes. Next, about 1 mL trifluoroacetic acid was added and the mixture stirred for about 14 hours. Afterwards, the mixture was poured into a solution of 5.6 g NaOH in about 300 mL water. The aqueous solution was extracted 3 times with about 150 mL each portions of ether. The organic layers were combined and dried with $MgSO_4$ and the volatiles removed on a rotovap. The resulting red viscous liquid was subjected to Kugelrohr at about 210° C. to give a faint yellow liquid which was $H_2$mnpm (FW 280.41). The first Kugelrohr yield was 1.438 g ($5.13 \times 10^{-3}$ moles, about 5.6%). The second Kugelrohr yield was 1.338 g ($4.77 \times 10^{-3}$ moles, about 5.2%). The third Kugelrohr yield was 1.415 g ($5.05 \times 10^{-3}$ moles, about 5.5%).

The synthesis of the catalyst was as follows. In an inert atmosphere dry box under purified $N_2$, a cold solution of 0.1753 g $H_2$mnpm ($6.25 \times 10^{-4}$ moles) was added to a cold solution of 148 µL $Ti(NMe_2)_4$ (FW 24.21 (d=0.947) 0.1402 g, $6.25 \times 10^{-4}$ moles) in ether. The yellow solution quickly turned orange. After about an hour, the volatiles were removed in vacuo, which left a red solid which was confirmed to be the catalyst by $^1$H NMR. The catalyst was also synthesized as follows. A cold solution of 1.26 g $H_2$mnpm ($4.49 \times 10^{-3}$ moles) was added to a cold solution of 1050 µL $Ti(NMe_2)_4$ (0.994 g, $4.43 \times 10^{-3}$ moles) in about 10 mL ether. The solution was stirred for about 2 hours and the volatiles were removed in vacuo. The catalyst was recrystallized from the ether. The yield was 0.5915 g ($9.94 \times 10^{-4}$ moles) catalyst which was a 22% yield.

A 3-component coupling to produce compound 1 is carried out in an inert atmosphere dry box under $N_2$ as follows. In a 40 mL pressure tube is loaded 1 mmol of the catalyst (2.0 M solution in toluene, 0.10 equiv.), aniline (1 equiv., 10 mmol, 0.911 mL), 1-hexyne (1 equiv., 10 mmol, 1.149 mL), and tert-butyl isocyanide (1 equiv., 10 mmol, 1.131 mL). The solution is diluted with toluene to 10 mL. The reaction is stirred at 100° C. for 24 hours. The solution is flushed through a pad of alumina (activated neutral) on a fritted funnel. Volatiles are removed by rotary evaporation, and distilled. Product 1 is obtained as a yellow oil by vacuum distillation (89–90° C., about 0.2 mmHg).

EXAMPLE 14

This example shows the synthesis of a norbornene copolymer comprising the $Ti(NMe_2)_2$(mnpm) catalyst. The reaction was performed in a box.

To a solution of 0.1351 g norbornene ($1.43 \times 10^{-3}$ moles) and 0.0674 g Ti(mnpm) $(NMe_2)_2$ ($1.58 \times 10^{-4}$ moles) in about 4 mL $CH_2Cl_2$ (11.1:1 norbornene: $Ti(NMe_2)_2$(mnpm) in a flask was added a solution of 0.0085 g (benzylidene)-bis(tricyclohexylphosphine)dichlororuthenium ($1.03 \times 10^{-5}$ moles, 149:1 M:I) in about 1 mL $CH_2Cl_2$. The reaction was stirred for about 3 hours which produced a viscous liquid. Then, about 0.5 mL ethyl vinyl ether was added and the mixture was stirred for about an hour. The resulting red liquid was dripped into stirring pentane in a flask to precipitate a red solid which was collected and dried in vacuo. The yield of copolymer was 0.152 g. The catalyst loading on the polymer was about 7.9% (0.0104 g catalyst in polymer, $2.45 \times 10^{-5}$ moles catalyst in polymer).

EXAMPLE 15

The norbornene-$Ti(NMe_2)_2$(mnpm) copolymer is used in a 3-component coupling reaction with 1-hexyne, tert-butyl isocyanide, and aniline to produce compound 1 as follows.

The 3-component coupling is carried out in an inert atmosphere dry box under $N_2$ as follows. In a 40 mL pressure tube is loaded 1 mmol of the catalyst (2.0 M solution in toluene, 0.10 equiv.), aniline (1 equiv., 10 mmol, 0.911 mL), 1-hexyne (1 equiv., 10 mmol, 1.149 mL), and tert-butyl isocyanide (1 equiv., 10 mmol, 1.131 mL). The solution is diluted with toluene to 10 mL. The reaction is stirred at 100° C. for 24 hours. The solution is flushed through a pad of alumina (activated neutral) on a fritted funnel. Volatiles are removed by rotary evaporation, and distilled. Product 1 is obtained as a yellow oil by vacuum distillation (89–90° C., about 0.2 mmHg)

EXAMPLE 16

This example shows another synthesis of a norbornene copolymer comprising the $Ti(NMe_2)_2$(mnpm) catalyst. The reaction was performed in an inert atmosphere dry box under purified $N_2$.

To a solution of 0.6873 g norbornene ($7.299 \times 10^{-3}$ moles) and 0.311 g Ti(mnpm) $(NMe_2)_2$ ($7.295 \times 10^{-4}$ moles) in about 40 mL $CH_2Cl_2$ (10:1 norbornene: $Ti(NMe_2)_2$(mnpm) in a flask was added a solution of 0.0597 g $Cl_2Ru(PCy_3)_2$ (=CHPh) in about 1 mL $CH_2Cl_2$ ($7.25 \times 10^{-5}$). The reaction was stirred for about 6 hours. Afterwards, about 0.5 mL ethyl vinyl ether was added and the mixture was stirred overnight. The resulting red liquid was dripped into vigorously stirring pentane in a flask to precipitate a dark red solid which was collected and dried in vacuo. The pentane/$CH_2Cl_2$ solution was pumped dry and the red solid dissolved in a minimum amount of $CH_2Cl_2$. This was then dripped into about 400 mL pentane in a flask. Stirring this mixture for several hours resulted in a more red solid forming at the bottom of the flask. This solid was collected and dried in vacuo. The yield of copolymer was 0.6680 g (66.9%). The theoretical catalyst loading on the polymer was about 9.13% (0.0104 g catalyst in polymer, $7.28 \times 10^{-3}$ moles catalyst in polymer).

EXAMPLE 17

The norbornene-$Ti(NMe_2)_2$(mnpm) copolymer of Example 17 is used in a 3-component coupling reaction with 1-hexyne, tert-butyl isocyanide, and aniline to produce compound 1 as follows.

The 3-component coupling is carried out in an inert atmosphere dry box under $N_2$ as follows. In a 40 mL pressure tube is loaded 1 mmol of the catalyst (2.0 M solution in toluene, 0.10 equiv.), aniline (1 equiv., 10 mmol, 0.911 mL), 1-hexyne (1 equiv., 10 mmol, 1.149 mL), and tert-butyl isocyanide (1 equiv., 10 mmol, 1.131 mL). The solution is diluted with toluene to 10 mL. The reaction is stirred at 100° C. for 24 hours. The solution is flushed through a pad of alumina (activated neutral) on a fritted funnel. Volatiles are removed by rotary evaporation, and distilled. Product 1 is obtained as a yellow oil by vacuum distillation (89–90° C., about 0.2 mmHg).

EXAMPLE 18

This example shows the synthesis of a polystyrene copolymer comprising the $Ti(NMe_2)_2$(mnpm) catalyst. The synthesis involved two steps (1) the synthesis of vinyl polystyrene comprising $Ru(PCy_3)_2Cl_2$ (ruthenated polystyrene) as an intermediate per Roberts et al., Organic Letts. 67: 1083–1086 (1999) and using the intermediate to make the polystyrene copolymer comprising the $Ti(NMe_2)_2$(mnpm).

In the first step, in an inert atmosphere dry box under purified $N_2$, to a suspension of 1.0131 g vinyl polystyrene (Novabiochem, $1.22 \times 10^{-3}$ moles) in about 10 mL of $CH_2Cl_2$ in a vial was added a solution of 0.0798 g $Cl_2Ru(PCy_3)_2$ (=CHPh) in about 2 mL $CH_2Cl_2$ ($9.70 \times 10^{-5}$ moles, 7.95% mole). The solution was stirred for about 8 hours and the resulting purple-brown solid was collected on a fritted funnel. The solid was washed well with $CH_2Cl_2$ and placed back into a vial and suspended in about 12 mL $CH_2Cl_2$.

In the second step, to the solid from above was added a solution of 0.6796 g norborene ($7.22 \times 10^{-3}$ moles) and 0.0655 g $Ti(NMe_2)_2$(mnpm) ($1.59 \times 10^{-4}$ moles, 47:1 norbornene: $Ti(NMe_2)_2$(mnpm). The solution and solid was stirred overnight, then filtered, washed twice with $CH_2Cl_2$ (30 mL each wash), washed twice with ether (30 mL each wash), washed twice with pentene (30 mL each wash), and dried in vacuo. The yield was 1.631 g (92.8% mass conversion). The $Ti(NMe_3)2$(mnpm) loading was $1.54 \times 10^{-4}$ mole Ti in 1.631 g of polymer ($9.44 \times 10^{-5}$ mole/g).

EXAMPLE 19

A 3-component coupling reaction using the polystyrene-Ti(mnpm) $(NMe_3)_2$ copolymer prepared in Example 20 is used to produce compound 1 as follows. All manipulations are performed in an inert atmosphere dry box under purified $N_2$.

In a 40 mL pressure tube is loaded 1 mmol of the copolymer (2.0 M solution in toluene, 0.10 equiv.), aniline (1 equiv., 10 mmol, 0.911 mL), 1-hexyne (1 equiv., 10 mmol, 1.149 mL), and tert-butyl isocyanide (1 equiv., 10 mmol, 1.131 mL). The solution is diluted with toluene to 10 mL. The reaction is stirred at 100° C. for 24 hours. The solution is flushed through a pad of alumina (activated neutral) on a fritted funnel. Volatiles are removed by rotary evaporation, and distilled. Product 1 is obtained as a yellow oil by vacuum distillation (89–90° C., about 0.2 mmHg)

EXAMPLE 20

A number of 3-component coupling reactions were performed with various combinations of amines, alkynes, and isonitriles. The amines were either phenylamine ($PhNh_2$) or cyclohexamine ($CyNH_2$); the alkynes were either 1-hexyne, 3-hexyne, 1,2-diphenylpropyne (PhCCPh), 1-phenylpropyne (PhCCMe), or phenylacetylene (PhCCH); and, the isonitriles were tert-butyl isocyanide (t-BuNC), cyclohexane isocyanide (CyNC), tetramethyl isocyanide (4MeNC), phenyl isocyanide, or $CH_3PhSO_2CH_2NC$.

Each reaction consisted of one of the above amines, one of the above alkynes, and one of the above isonitriles. All of the reactions contained 1 mmole of the amine and 1 mmole of the alkyne. The amount of the isonitrile varied from 1.2 mmole to 1.0 mmole. Each reaction contained 10% $Ti(NMe_2)_2$(dpma) was performed at 100° C. as described in Examples 2–10. Afterwards, an aliquot of the reaction was placed in 227 μL dodecane and analyzed by HPLC. The results are shown in Table 2.

TABLE 2

| | | | | Product yield (%) | |
|---|---|---|---|---|---|
| No. | Amine | Alkyne | Isonitrile | 24 hr | 48 hr |
| 1 | $PhNH_2$ | 3-hexyne | t-BuNC | 24 | 32 |
| 2 | $PhNH_2$ | PhCCPh | t-BuNC | 22 | 30 |
| 3 | $PhNH_2$ | PhCCMe | t-BuNC | 67 | 98 |
| 4 | $CyNH_2$ | 3-hexyne | t-BuNC | Trace | Trace |
| 5 | $CyNH_2$ | PhCCPh | t-BuNC | Trace | Trace |
| 6 | $CyNH_2$ | PhCCPh | t-BuNC | Trace | Trace |
| 7 | $PhNH_2$ | 1-hexyne | CyNC | | |
| 8 | $PhNH_2$ | 3-hexyne | CyNC | | |
| 9 | $PhNH_2$ | PhCCPh | CyNC | | |
| 10 | $PhNH_2$ | PhCCMe | CyNC | | |
| 11 | $PhNH_2$ | PhCCMe | CyNC | | |
| 12 | $CyNH_2$ | 1-hexyne | CyNC | | |
| 13 | $CyNH_2$ | 3-hexyne | CyNC | | |
| 14 | $CyNH_2$ | PhCCPh | CyNC | | |
| 15 | $PhNH_2$ | 1-hexyne | 4MeNC | | |
| 16 | $PhNH_2$ | 3-hexyne | 4MeNC | 54 | 64 |
| 17 | $PhNH_2$ | PhCCPh | 4MeNC | 31 | 43 |
| 18 | $PhNH_2$ | PhCCMe | 4MeNC | 91 | |
| 19 | $CyNH_2$ | 1-hexyne | 4MeNC | 61 | 67 |
| 20 | $CyNH_2$ | 3-hexyne | 4MeNC | 40 | 53 |
| 21 | $CyNH_2$ | PhCCPh | 4MeNC | | 21 |
| 22 | $CyNH_2$ | PhCCMe | 4MeNC | | 29 |
| 23 | $PhNH_2$ | 1-hexyne | $CH_3PhSO_2CH_2NC$ | 0 | 0 |
| 24 | $PhNH_2$ | 3-hexyne | $CH_3PhSO_2CH_2NC$ | 0 | 0 |
| 25 | $PhNH_2$ | PhCCH | $CH_3PhSO_2CH_2NC$ | 0 | 0 |
| 26 | $PhNH_2$ | PhCCMe | $CH_3PhSO_2CH_2NC$ | 0 | 0 |
| 27 | $CyNH_2$ | 1-hexyne | $CH_3PhSO_2CH_2NC$ | 0 | |
| 28 | $CyNH_2$ | 3-hexyne | $CH_3PhSO_2CH_2NC$ | 0 | |
| 29 | $CyNH_2$ | PhCCH | $CH_3PhSO_2CH_2NC$ | 0 | |
| 30 | $CyNH_2$ | PhCCMe | $CH_3PhSO_2CH_2NC$ | 0 | |
| 31 | $CyNH_2$ | 1-hexyne | t-BuNC | 56 | |
| 32 | $CyNH_2$ | PhCCH | t-BuNC | 85 | |
| 33 | $PhNH_2$ | 3-hexyne | t-BuNC | 41 | 22 |
| 34 | $PhNH_2$ | PhCCPh | t-BuNC | 0 | 0 |
| 35 | $PhNH_2$ | PhCCH | t-BuNC | | |
| 36 | $PhNH_2$ | PhCCH | 4MeNC | | |
| 37 | $PhNH_2$ | PhCCH | 4MeNC | | |
| 38 | $PhNH_2$ | 1-hexyne | t-BuNC | | |
| 39 | $CyNH_2$ | PhCCH | PhNC | 0 | 0 |

While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

I claim:

1. A process for producing a substituted α,β-unsaturated β-iminoamine which comprises:
reacting a primary amine, an alkyne, and an isonitrile in the presence of a catalytic complex comprising a transition metal selected from the group consisting of titanium, zirconium, hafnium, and unnilquadium and a chelating ligand in a solvent which does not interfere with the reaction for coupling the nitrogen of the primary amine to a first carbon of the triple carbon-carbon bond of the alkyne and coupling the nitrile carbon of the isonitrile to the second carbon of the triple carbon-carbon bond of the alkyne to produce the substituted iminoamine.

2. The process of claim 1 wherein the primary amine is selected from the group consisting of aryl amines, cyclic amines, alkylamines, substituted aryl amines, substituted cyclic amines, substituted alkylamines, and combinations thereof.

3. The process of claim 1 wherein the alkyne is selected from the group of consisting of terminal alkynes, internal alkynes, substituted terminal alkynes, substituted internal alkynes, and combinations thereof.

4. The process of claim 1 wherein the isonitrile is selected from the group consisting of alkyl isonitriles, aryl nitriles, substituted alkyl isonitriles, substituted aryl nitriles, and combinations thereof.

5. The process of claim 1 wherein the ligand is selected from the group consisting of cyclopentadienyl, thiolate, pyrrolyl, amido, guandininate, and derivatives thereof.

6. The process of claim 1 wherein the ligand is a chelating pyrrolyl-based ligand selected from the group consisting of N,N-di(pyrrolyl-α-methyl)-N-methylamine (dpma), 5,5-dimethyl-dipyrrolylmethane) (dmpm), 5,5-dipropyl-dipyrrolylmethane (dppm), 5-methyl-5-ethylene-bicyclo[2.1.1]hept-2-ene-dipyrrolylmethane (mnpm), and derivatives thereof.

7. The process of claim 1 wherein the catalytic complex is selected from the group consisting of bis(dimethylamido)(N,N-di(pyrrolyl-α-methyl)-N-methylamine)titanium (Ti(NMe$_2$)$_2$(dpma)), (bis(dimethylamido)(5,5-dipropyl-dipyrrolylmethane)titanium (Ti(NMe$_2$)$_2$(dppm)), bis(dimethylamido)(5,5-dimethyl-dipyrrolylmethane)titanium (Ti(NMe$_2$)$_2$(dmpm)), bis(dimethylamido) 5-methyl-5-ethylene-bicyclo[2.1.1]hept-2-ene-dipyrrolylmethane (Ti(NMe$_2$)$_2$(mnpm)), and derivatives thereof.

8. The process of claim 1 wherein the catalytic complex is anchored to a surface of a substrate.

9. The process of claim 8 wherein the substrate is glass or a polymer.

10. The process of claim 8 wherein the substrate is selected from the group consisting of norbornene, polystyrene, and derivatives thereof.

11. The process of any one of claim 8, 9, or 10 wherein the catalytic complex is selected from the group consisting of bis(dimethylamido)(N,N-di(pyrrolyl-α-methyl)-N-methylamine)titanium (Ti(NMe$_2$)$_2$(dpma)), (bis(dimethylamido)(5,5-dipropyl-dipyrrolylmethane)titanium (Ti(NMe$_2$)$_2$(dppm)), bis(dimethylamido)(5,5-dimethyl-dipyrrolylmethane)titanium (Ti(NMe$_2$)$_2$(dmpm)), bis(dimethylamido) 5-methyl-5-ethylene-bicyclo[2.1.1]hept-2-ene-dipyrrolylmethane (Ti(NMe$_2$)$_2$(mnpm)), and derivatives thereof.

12. A process for producing a substituted α,β-unsaturated β-iminoamine which comprises:
reacting a primary amine, an alkyne, and an isonitrile in the presence of a catalytic complex comprising titanium and a chelating ligand in a solvent which does not interfere with the reaction for coupling the nitrogen of the primary amine to a first carbon of the triple carbon-carbon bond of the alkyne and coupling nitrile carbon of the isonitrile to the second carbon of the triple carbon-carbon bond of the alkyne to produce the substituted α,β-unsaturated β-iminoamine.

13. The process of claim 12 wherein the primary amine is selected from the group consisting of aryl amines, cyclic amines, alkylamines, substituted aryl amines, substituted cyclic amines, substituted alkylamines, and combinations thereof.

14. The process of claim 12 wherein the alkyne is selected from the group of consisting of terminal alkynes, internal alkynes, substituted terminal alkynes, substituted internal alkynes, and combinations thereof.

15. The process of claim 12 wherein the isonitrile is selected from the group consisting of alkyl isonitriles, aryl nitriles, substituted alkyl isonitriles, substituted aryl nitriles, and combinations thereof.

16. The process of claim 12 wherein the ligand is selected from the group consisting of cyclopentadienyl, thiolate, pyrrolyl, amido, guandininate, and derivatives thereof.

17. The process of claim 13 wherein the ligand is a chelating pyrrolyl-based ligand selected from the group consisting of N,N-di(pyrrolyl-α-methyl)-N-methylamine (dpma), 5,5-dimethyl-dipyrrolylmethane) (dmpm), 5,5-dipropyl-dipyrrolylmethane (dppm), 5-methyl-5-ethylene-bicyclo[2.1.1]hept-2-ene-dipyrrolylmethane (mnpm), and derivatives thereof.

18. The process of claim 12 wherein the catalytic complex is selected from the group consisting of bis(dimethylamido)(N,N-di(pyrrolyl-α-methyl)-N-methylamine)titanium (Ti(NMe$_2$)$_2$(dpma)), (bis(dimethylamido)(5,5-dipropyl-dipyrrolylmethane)titanium (Ti(NMe$_2$)$_2$(dppm)), bis(dimethylamido)(5,5-dimethyl-dipyrrolylmethane)titanium (Ti(NMe$_2$)$_2$(dmpm)), bis(dimethylamido) 5-methyl-5-ethylene-bicyclo[2.1.1]hept-2-ene-dipyrrolylmethane (Ti(NMe$_2$)$_2$(mnpm)), and derivatives thereof.

19. The process of claim 12 wherein the catalytic complex is anchored to a surface of a substrate.

20. The process of claim 19 wherein the substrate is glass or a polymer.

21. The process of claim 19 wherein the substrate is selected from the group consisting of norbornene, polystyrene, and derivatives thereof.

22. The process of any one of claim 19, 20, or 21 wherein the catalytic complex is selected from the group consisting of bis(dimethylamido)(N,N-di(pyrrolyl-α-methyl)-N-methylamine)titanium (Ti(NMe$_2$)$_2$(dpma)), (bis(dimethylamido)(5,5-dipropyl-dipyrrolylmethane)titanium (Ti(NMe$_2$)$_2$(dppm)), bis(dimethylamido)(5,5-dimethyl-dipyrrolylmethane)titanium (Ti(NMe$_2$)$_2$(dmpm)), bis(dimethylamido) 5-methyl-5-ethylene-bicyclo[2.1.1]hept-2-ene-dipyrrolylmethane (Ti(NMe$_2$)$_2$(mnpm)), and derivatives thereof.

23. A process for producing a library of substituted α,β-unsaturated β-iminoamines which comprises:
reacting one or more primary amines, one or more alkynes, and one or more isonitriles in the presence of a catalytic complex comprising a transition metal selected from the group consisting of titanium, zirconium, hafnium, and unnilquadium and a chelating ligand in a solvent which does not interfere with the reaction for coupling the nitrogen of the primary amine to a first carbon of the triple carbon-carbon bond of the alkyne and coupling nitrile carbon of the isonitrile to the second carbon of the triple carbon-carbon bond of the alkyne to produce the library of substituted iminoamines.

24. The process of claim 23 wherein the primary amines are selected from the group consisting of aryl amines, cyclic amines, alkylamines, substituted aryl amines, substituted cyclic amines, substituted alkylamines, and combinations thereof.

25. The process of claim 23 wherein the alkynes are selected from the group of consisting of terminal alkynes, internal alkynes, substituted terminal alkynes, substituted internal alkynes, and combinations thereof.

26. The process of claim 23 wherein the substituted isonitriles are selected from the group consisting of alkyl isonitriles, aryl nitriles, substituted alkyl isonitriles, substituted aryl nitriles, and combinations thereof.

27. The process of claim 23 wherein the ligand is selected from the group consisting of cyclopentadienyl, thiolate, pyrrolyl, amido, guandininate, and derivatives thereof.

28. The process of claim 23 wherein the ligand is a chelating pyrrolyl-based ligand selected from the group consisting of N,N-di(pyrrolyl-α-methyl)-N-methylamine (dpma), 5,5-dimethyl-dipyrrolylmethane) (dmpm), 5,5-dipropyl-dipyrrolylmethane (dppm), 5-methyl-5-ethylene-bicyclo[2.1.1]hept-2-ene-dipyrrolylmethane (mnpm), and derivatives thereof.

29. The process of claim 23 wherein the catalytic complex is selected from the group consisting of bis(dimethylamido)(N,N-di(pyrrolyl-α-methyl)-N-methylamine)titanium (Ti(NMe$_2$)$_2$(dpma)), (bis(dimethylamido)(5,5-dipropyl-dipyrrolylmethane)titanium (Ti(NMe$_2$)$_2$(dppm)), bis(dimethylamido)(5,5-dimethyl-dipyrrolylmethane)titanium (Ti(NMe$_2$)$_2$(dmpm)), bis(dimethylamido) 5-methyl-5-ethylene-bicyclo[2.1.1]hept-2-ene-dipyrrolylmethane (Ti(NMe$_2$)$_2$(mnpm)), and derivatives thereof.

30. The process of claim 23 wherein the catalytic complex is anchored to a surface of a substrate.

31. The process of claim 30 wherein the substrate is glass or a polymer.

32. The process of claim 30 wherein the substrate is selected from the group consisting of norbornene, polystyrene, and derivatives thereof.

33. The process of any one of claim 30, 31, or 32 wherein the catalytic complex is selected from the group consisting of bis(dimethylamido)(N,N-di(pyrrolyl-α-methyl)-N-methylamine)titanium (Ti(NMe$_2$)$_2$(dpma)), (bis(dimethylamido)(5,5-dipropyl-dipyrrolylmethane)titanium (Ti(NMe$_2$)$_2$(dppm)), bis(dimethylamido)(5,5-dimethyl-dipyrrolylmethane)titanium (Ti(NMe$_2$)$_2$(dmpm)), bis(dimethylamido) 5-methyl-5-ethylene-bicyclo[2.1.1]hept-2-ene-dipyrrolylmethane (Ti(NMe$_2$)$_2$(mnpm)), and derivatives thereof.

34. A process for producing a substituted α,β-unsaturated β-iminoamine which comprises:
reacting a primary amine, an alkyne, and an isonitrile in the presence of a catalytic complex comprising a transition metal selected from the group consisting of titanium, zirconium, hafnium, and unnilquadium and a chelating ligand selected from the group consisting of cyclopentadienyl, thiolate, pyrrolyl, amido, guandininate, and derivatives thereof in a solvent which does not interfere with the reaction for coupling the nitrogen of the primary amine to a first carbon of the triple carbon-carbon bond of the alkyne and coupling nitrile carbon of the isonitrile to the second carbon of the triple carbon-carbon bond of the alkyne to produce the substituted α,β-unsaturated β-iminoamine.

35. The process of claim 34 wherein the primary amine is selected from the group consisting of aryl amines, cyclic amines, alkylamines, substituted aryl amines, substituted cyclic amines, substituted alkylamines, and combinations thereof.

36. The process of claim 34 wherein the alkyne is selected from the group of consisting of terminal alkynes, internal alkynes, substituted terminal alkynes, substituted internal alkynes, and combinations thereof.

37. The process of claim 34 wherein the isonitrile is selected from the group consisting of alkyl isonitriles, aryl nitriles, substituted alkyl isonitriles, substituted aryl nitriles, and combinations thereof.

38. The process of claim 34 wherein the ligand is a chelating pyrrolyl-based ligand selected from the group consisting of N,N-di(pyrrolyl-α-methyl)-N-methylamine (dpma), 5,5-dimethyl-dipyrrolylmethane) (dmpm), 5,5-dipropyl-dipyrrolylmethane (dppm), 5-methyl-5-ethylene-bicyclo[2.1.1]hept-2-ene-dipyrrolylmethane (mnpm), and derivatives thereof.

39. The process of claim 34 wherein the catalytic complex is selected from the group consisting of bis(dimethylamido)(N,N-di(pyrrolyl-α-methyl)-N-methylamine)titanium (Ti(NMe$_2$)$_2$(dpma)), (bis(dimethylamido)(5,5-dipropyl-dipyrrolylmethane)titanium (Ti(NMe$_2$)$_2$(dppm)) bis(dimethylamido)(5,5-dimethyl-dipyrrolylmethane)titanium (Ti(NMe$_2$)$_2$(dmpm)), bis(dimethylamido) 5-methyl-5-ethylene-bicyclo[2.1.1]hept-2-ene-dipyrrolylmethane (Ti(NMe$_2$)$_2$(mnpm)), and derivatives thereof.

40. The process of claim 34 wherein the catalytic complex is anchored to a surface of a substrate.

41. The process of claim 40 wherein the substrate is glass or a polymer.

42. The process of claim 40 wherein the substrate is selected from the group consisting of norbornene, polystyrene, and derivatives thereof.

43. The process of any one of claim 40, 41, or 42 wherein the catalytic complex is selected from the group consisting of bis(dimethylamido)(N,N-di(pyrrolyl-α-methyl)-N-methylamine)titanium (Ti(NMe$_2$)$_2$(dpma)), (bis(dimethylamido)(5,5-dipropyl-dipyrrolylmethane)titanium (Ti(NMe$_2$)$_2$(dppm)), bis(dimethylamido)(5,5-dimethyl-dipyrrolylmethane)titanium (Ti(NMe$_2$)$_2$(dmpm)), bis(dimethylamido) 5-methyl-5-ethylene-bicyclo[2.1.1]hept-2-ene-dipyrrolylmethane (Ti(NMe$_2$)$_2$(mnpm)), and derivatives thereof.

44. A process for producing a substituted α,β-unsaturated β-iminoamine which comprises:
reacting a primary amine, an alkyne, and an isonitrile in the presence of a catalytic complex comprising a transition metal selected from the group consisting of titanium, zirconium, hafnium, and unnilquadium and a chelating ligand anchored to the surface of a substrate in a solvent which does not interfere with the reaction for coupling the nitrogen of the primary amine to a first carbon of the triple carbon-carbon bond of the alkyne and coupling nitrile carbon of the isonitrile to the second carbon of the triple carbon-carbon bond of the alkyne to produce the substituted α,β-unsaturated β-iminoamine.

45. The process of claim 44 wherein the primary amine is selected from the group consisting of aryl amines, cyclic amines, alkylamines, substituted aryl amines, substituted cyclic amines, substituted alkylamines, and combinations thereof.

46. The process of claim 44 wherein the alkyne is selected from the group of consisting of terminal alkynes, internal alkynes, substituted terminal alkynes, substituted internal alkynes, and combinations thereof.

47. The process of claim 44 wherein the isonitrile is selected from the group consisting of alkyl isonitriles, aryl nitriles, substituted alkyl isonitriles, substituted aryl nitriles, and combinations thereof.

48. The process of claim 44 wherein the ligand is selected from the group consisting of cyclopentadienyl, thiolate, pyrrolyl, amido, guandininate, and derivatives thereof.

49. The process of claim 44 wherein the ligand is a chelating pyrrolyl-based ligand selected from the group consisting of N,N-di(pyrrolyl-α-methyl)-N-methylamine (dpma), 5,5-dimethyl-dipyrrolylmethane) (dmpm), 5,5-dipropyl-dipyrrolylmethane (dppm), 5-methyl-5-ethylene-bicyclo[2.1.1]hept-2-ene-dipyrrolylmethane (mnpm), and derivatives thereof.

50. The process of claim 44 wherein the catalytic complex is selected from the group consisting of bis(dimethylamido) (N,N-di(pyrrolyl-α-methyl)-N-methylamine)titanium (Ti(NMe$_2$)$_2$(dpma)), (bis(dimethylamido)(5,5-dipropyl-dipyrrolylmethane)titanium (Ti(NMe$_2$)$_2$(dppm)), bis(dimethylamido)(5,5-dimethyl-dipyrrolylmethane)titanium (Ti(NMe$_2$)$_2$(dmpm)), bis(dimethylamido) 5-methyl-5-ethylene-bicyclo[2.1.1]hept-2-ene-dipyrrolylmethane (Ti(NMe$_2$)$_2$(mnpm)), and derivatives thereof.

51. The process of claim 44 wherein the substrate is glass or a polymer.

52. The process of claim 51 wherein the substrate is selected from the group consisting of norbornene, polystyrene, and derivatives thereof.

53. The process of claim 51 or 52 wherein the catalytic complex is selected from the group consisting of bis(dimethylamido)(N,N-di(pyrrolyl-α-methyl)-N-methylamine)titanium (Ti(NMe$_2$)$_2$(dpma)), (bis(dimethylamido)(5,5-dipropyl-dipyrrolylmethane)titanium (Ti(NMe$_2$)$_2$(dppm)), bis(dimethylamido)(5,5-dimethyl-dipyrrolylmethane)titanium (Ti(NMe$_2$)$_2$(dmpm)), bis(dimethylamido) 5-methyl-5-ethylene-bicyclo[2.1.1]hept-2-ene-dipyrrolylmethane (Ti(NMe$_2$)$_2$(mnpm)), and derivatives thereof.

54. A compound which is (bis(dimethylamido)(5,5-dipropyl-dipyrrolylmethane)titanium (Ti(NMe$_2$)$_2$(dppm)).

55. A compound which is bis(dimethylamido) 5-methyl-5-ethylene-bicyclo[2.1.1]hept-2-ene-dipyrrolylmethane (Ti(NMe$_2$)$_2$(mnpm)).

56. A compound selected from the group consisting of

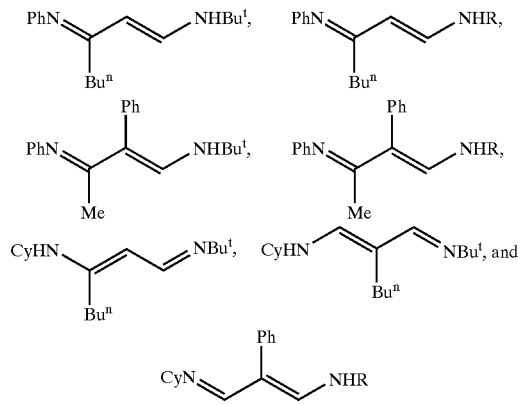

wherein Ph is phenyl, Me is methyl, Cy is cyclohexyl, Bu$^t$ is t-butyl, and Bu$^n$ is n-butyl wherein R is selected from the group consisting of linear or branched alkyl and cycloalkyl.

* * * * *

UNITED STATES PATENT AND TRADEMARK OFFICE
CERTIFICATE OF CORRECTION

PATENT NO. : 6,861,559 B2
DATED : March 1, 2005
INVENTOR(S) : Aaron L. Odom

It is certified that error appears in the above-identified patent and that said Letters Patent is hereby corrected as shown below:

Column 3,
Line 16, "aryl nitrites" should be -- aryl nitriles --.

Column 4,
Lines 14 and 15, "aryl nitrites" should be -- aryl nitriles --.

Column 5,
Lines 7 and 8, "aryl nitrites" should be -- aryl nitriles --.

Column 12,
Line 37, "aryl nitrites" should be -- aryl nitriles --.

Column 23,
Line 55, "Ti (NMe$_3$)2(mnpm)" should be -- Ti (NMe$_3$)$_2$(mnpm) --.

Column 25,
Line 38, "of claim 8, 9, or 10" should be -- of Claims 8, 9, or 10 --.

Column 26,
Line 28, "of claim 13" should be -- of Claim 12 --.

Column 27,
Line 47, "claim 30, 31, or 32" should be -- Claims 30, 31, or 32 --.

Column 28,
Line 39, "claim 40, 41, or 42" should be -- Claims 40, 41, or 42 --.

Signed and Sealed this

Seventeenth Day of May, 2005

JON W. DUDAS
*Director of the United States Patent and Trademark Office*